US012201645B2

United States Patent
Bussolari et al.

(10) Patent No.: US 12,201,645 B2
(45) Date of Patent: Jan. 21, 2025

(54) METHODS OF TREATING MYELODYSPLASTIC SYNDROME

(71) Applicant: Geron Corporation, Menlo Park, CA (US)

(72) Inventors: Jacqueline Cirillo Bussolari, Raritan, NJ (US); Fei Huang, North Wales, PA (US); Aleksandra Rizo, Raritan, NJ (US)

(73) Assignee: Geron Corporation, Foster City, CA (US)

( * ) Notice: Subject to any disclaimer, the term of this patent is extended or adjusted under 35 U.S.C. 154(b) by 1037 days.

(21) Appl. No.: 16/696,103

(22) Filed: Nov. 26, 2019

(65) Prior Publication Data

US 2020/0171072 A1    Jun. 4, 2020

Related U.S. Application Data

(60) Provisional application No. 62/860,557, filed on Jun. 12, 2019, provisional application No. 62/811,271, (Continued)

(51) Int. Cl.
*A61K 31/7125*    (2006.01)
*A61K 31/4439*    (2006.01)
(Continued)

(52) U.S. Cl.
CPC ...... *A61K 31/7125* (2013.01); *A61K 31/4439* (2013.01); *A61K 31/706* (2013.01); *A61P 35/00* (2018.01); *G01N 33/573* (2013.01)

(58) Field of Classification Search
CPC ........... A61K 31/7125; A61K 31/4439; G01N 2333/9128; G01N 2800/52; A61P 35/00
See application file for complete search history.

(56) References Cited

U.S. PATENT DOCUMENTS 5,583,016 A    12/1996    Villeponteau et al.
5,656,638 A    8/1997    Gaeta et al.
(Continued)

FOREIGN PATENT DOCUMENTS

CN    101220044    7/2008
JP    2016537423    12/2016
(Continued)

OTHER PUBLICATIONS

Tefferi et al (Blood Cancer Journal (Mar. 2016) 6, e405; doi:10.1038/bcj.2016.13, 2 pages).*

(Continued)

*Primary Examiner* — Terra C Gibbs
(74) *Attorney, Agent, or Firm* — Rudy J. Ng; Melissa Nakamoto; Bozicevic, Field & Francis LLP

(57) ABSTRACT

Methods of monitoring therapeutic efficacy in a subject with MDS are provided. Also provided is a method of identifying a subject with myelodysplastic syndrome (MDS) for treatment with a telomerase inhibitor, and methods of treating MDS. The subject methods can include administering to the subject an effective amount of a telomerase inhibitor and assessing the hTERT expression levels in a biological sample obtained from the subject. In some cases, a 50% or greater reduction in hTERT expression level identifies a subject who has an increased likelihood of benefiting from treatment with the telomerase inhibitor. The subject can be naive to treatment with a HMA, lenalidomide, or both. In some cases, the subject is classified as having low or intermediate-1 IPSS risk MDS and/or MDS relapsed/refractory to Erythropoiesis-Stimulating Agent (ESA). In some instances, the telomerase inhibitor is imetelstat sodium.

46 Claims, 9 Drawing Sheets

Related U.S. Application Data filed on Feb. 27, 2019, provisional application No. 62/772,861, filed on Nov. 29, 2018.

(51) Int. Cl.
*A61K 31/706* (2006.01)
*A61P 35/00* (2006.01)
*G01N 33/573* (2006.01)

(56) References Cited

U.S. PATENT DOCUMENTS

| | | | |
|---|---|---|---|
| 5,695,932 | A | 12/1997 | West et al. |
| 5,760,062 | A | 6/1998 | Gaeta et al. |
| 5,767,278 | A | 6/1998 | Gaeta et al. |
| 5,770,613 | A | 6/1998 | Gaeta et al. |
| 5,840,490 | A | 11/1998 | Bacchetti et al. |
| 5,863,936 | A | 1/1999 | Gaeta et al. |
| 5,952,490 | A | 9/1999 | Hanecak et al. |
| 5,958,680 | A | 9/1999 | Villeponteau et al. |
| 6,261,836 | B1 | 7/2001 | Cech et al. |
| 6,331,399 | B1 | 12/2001 | Monia et al. |
| 6,368,789 | B1 | 4/2002 | West et al. |
| 6,444,650 | B1 | 9/2002 | Cech et al. |
| 6,548,298 | B2 | 4/2003 | Villeponteau et al. |
| 6,608,036 | B1 | 8/2003 | Gryaznov et al. |
| 7,067,497 | B2 | 6/2006 | Hanecak et al. |
| 7,321,029 | B2 | 1/2008 | Gryaznov et al. |
| 7,485,717 | B2 | 2/2009 | Gryaznov et al. |
| 7,494,982 | B2 | 2/2009 | Gryaznov et al. |
| 7,563,618 | B2 | 7/2009 | Gryaznov et al. |
| 7,989,428 | B2 | 8/2011 | Go et al. |
| 7,989,603 | B2 | 8/2011 | Gryaznov et al. |
| 7,998,938 | B2 | 8/2011 | Moore et al. |
| 8,153,604 | B2 | 4/2012 | Deen et al. |
| 8,377,644 | B2 | 2/2013 | Gryaznov et al. |
| 8,440,635 | B2 | 5/2013 | Gryaznov et al. |
| 8,906,615 | B2 | 12/2014 | Gryaznov et al. |
| 9,133,233 | B2 | 9/2015 | Gryaznov et al. |
| 9,375,485 | B2 * | 6/2016 | Stuart ............ B82Y 5/00 |
| 9,388,415 | B2 | 7/2016 | Gryaznov |
| 9,404,112 | B2 | 8/2016 | Gryaznov |
| 11,123,359 | B2 | 9/2021 | Tefferi |
| 2005/0113325 | A1 | 5/2005 | Gryaznov et al. |
| 2005/0282893 | A1 | 12/2005 | Au et al. |
| 2006/0009636 | A1 | 1/2006 | Gryaznov et al. |
| 2006/0166221 | A1 | 7/2006 | Bahou et al. |
| 2007/0015723 | A1 | 1/2007 | Hanecak et al. |
| 2007/0224598 | A1 | 9/2007 | Chang |
| 2007/0270363 | A1 | 11/2007 | Bennett et al. |
| 2009/0162849 | A1 | 6/2009 | Vainchenker et al. |
| 2009/0227681 | A1 | 9/2009 | Dimock |
| 2010/0104586 | A1 | 4/2010 | Tressler et al. |
| 2011/0263685 | A1 | 10/2011 | Harley et al. |
| 2012/0032072 | A1 | 2/2012 | Quarmby |
| 2012/0322072 | A1 | 12/2012 | Nygren |
| 2013/0253042 | A1 | 9/2013 | Gryaznov et al. |
| 2014/0155465 | A1 | 6/2014 | Bassett et al. |
| 2014/0163090 | A1 | 6/2014 | Stuart et al. |
| 2014/0193518 | A1 | 7/2014 | Sayeski et al. |
| 2014/0329890 | A1 | 11/2014 | Gryaznov et al. |
| 2015/0005250 | A1 | 1/2015 | Rollison et al. |
| 2015/0017119 | A1 | 1/2015 | Fantl et al. |
| 2015/0299232 | A1 | 10/2015 | Gryaznov et al. |
| 2015/0342982 | A1 | 12/2015 | Stuart et al. |
| 2016/0287625 | A1 | 10/2016 | Tefferi |
| 2017/0051287 | A1 | 2/2017 | Stuart et al. |
| 2018/0036336 | A1 | 2/2018 | Huang et al. |

FOREIGN PATENT DOCUMENTS

| | | |
|---|---|---|
| WO | 2001/018015 | 3/2001 |
| WO | WO 2002/077184 | 10/2002 |
| WO | WO 2004/029277 | 4/2004 |
| WO | WO 2008/054711 | 4/2004 |
| WO | 2005023994 | 3/2005 |
| WO | WO 2006/113426 | 10/2006 |
| WO | WO 2007/016354 | 2/2007 |
| WO | WO 2014/085632 | 5/2008 |
| WO | WO 2008112129 | 9/2008 |
| WO | WO 2010045245 | 4/2010 |
| WO | WO2011017096 | 2/2011 |
| WO | WO 2011098901 | 8/2011 |
| WO | WO 2013059738 | 4/2013 |
| WO | 2014088785 | 6/2014 |
| WO | WO 2015/069758 | 6/2014 |
| WO | WO2014160071 | 10/2014 |
| WO | WO2018026646 | 2/2018 |
| WO | 2019023667 | 1/2019 |

OTHER PUBLICATIONS

Mosoyan et al. (Leukemia, 2017, 31:2458-2467).*
Patnaik et al (Am. J. Hematol. 90(6): 550-559, 2015).*
Haase et al. (Blood 110(13):4385-4395, 2007).*
Paulsson et al. (Pathol Biol (Paris) 2007; 55: 37-48).*
Fragkiadaki et al. (Molecular Medicine Reports, 2022 vol. 25:158, pp. 1-11).*
Mascarenhas et al. (Abstract 347. Session 634, Presented at American Society of Hematology National Conference 2020).*
Wayne Kuznar (Jan. 19, 2021, downloaded from https://www.onclive.com/view/imetelstat-disease-modifying-activity-relapsed-refractory-myelofibrosis-shown-effect-telomerase-activity on Nov. 28, 2023).*
Santini et al. (Blood (2021) 138 (Supplement 1):2598-2600).*
Fialkow (1981) "Evidence that essential thrombocythemia is a clonal disorder with origin in a multipotent stem cell" Blood; 58:916-919.
European Search Report for EP 13861008.4 dated Aug. 22, 2016.
International Search Report for PCT/US2013/070437 dated Jan. 22, 2014.
The Merck Manual 18th Edition, Japanese language version, Nikkei Business Publications, Inc., Apr. 25, 2007, p. 1159-1162.
Asai, et al., (2003), "A Novel Telomerase Template Antagonist (GRN163) as a Potential Anticancer Agent", Cancer Research, vol. 63, pp. 3931-3939.
Baerlocher, et al., (2015), "Telomerase Inhibitor Imetelstat in Patients with Essential Thrombocythemia", The New England Journal of Medicine, vol. 373, pp. 920-928.
Fenaux, et al., (2011), "A randomized phase 3 study of lenalidomide versus placebo in RBC transfusion-dependent patients with Low-/Intermediate-1-risk myelodysplastic syndromes with del5q", Blood, vol. 118, No. 14, pp. 3765-3776.
Fenaux, et al., (2013), "How we treat lower-risk myelodysplastic syndromes", Blood, vol. 121, No. 21, pp. 4280-4286.
Greenberg, et al., (2012), "Revised International Prognostic Scoring System for Myelodysplastic Syndromes", Blood, vol. 120, No. 12, pp. 2454-2465.
Gryaznov, (2010), "Oligonucleotide N3' → P5' Phosphoramidates and Thio-Phosphoramidates as Potential Therapeutic Agents", Chem. Biodivers., vol. 7, pp. 477-493.
Herbert, et al., (2005), "Lipid modification of GRN163, an N3' → P5' thio-phosphoramidate oligonucleotide, enhances the potency of telomerase inhibition", Oncogene, vol. 24, pp. 5262-5268.
Palma, et al. (2013), "Telomere length and expression of human telomerase reverse transcriptase splice variants in chronic lymphocytic leukemia", Experimental Hematology, vol. 41, pp. 615-626.
Tefferi, et al., (2015), "A Pilot Study of the Telomerase Inhibitor imetelstat for Myelofibrosis", The New England Journal of Medicine, Vo. 373, pp. 908-919.
Vardiman, et al., (2009), "The 2008 revision of the World Health Organization (WHO) classification of myeloid neoplasms and acute leukemia: rationale and Important changes", Blood, vol. 114, No. 5, pp. 937-951.
Adams (1983) "Hindered dialkylamino nucleoside phosphite reagents in the synthesis of two DNA 51-mers" J. Am. Chem. Soc. 105, 661-663.
Baerlocher, et al., "Imetelstat rapidly Induces and Maintains Substantial Hematologic and Molecular Responses in Patients with

(56) References Cited

OTHER PUBLICATIONS

Essential Thrombocythemia (ET) who are Refractory or Intolerant to Prior Therapy:Preliminary Phase II Results", Blood, (ASH Meeting Abstracts), vol. 120, No. 21:179, 7 pages, 2012.
Baerlocher, et al., "Imetelstat: A Novel Approach with Robust Hematologic and Molecular Responses in a Phase 2 study in Patients with Essential Thrombocythemia (ET) who are Refractory or Intolerant to Prior Therapy, Hematologica" 98(s1) Abstract S112, 2012.
Barbui, et al., "Perspectives on thrombosis in essential thrombocythemia and polycythemia vera: is leukocytosis a causative factor?", Blood 114, 759-763, 2009.
Barosi, et al., "Response criteria for essential thrombocytemia and polycythemia vera: result of a European LeukemiaNet consensus conference", Blood, 113(20), 4829-4833, 2009.
Baxter et al., "Acquired mutation of the tyrosine kinase JAK2 in human myeloproliferative disorders", Lancet 365, 1054-1061, 2005.
Beaucage, "Deoxynucleoside phosphoramidites—A new class of key intermediates of deoxypolynucoleotide synthesis", Tetra. Lett. 22, p. 1859, 1981.
Beer, et al., "How I treat essential throbocythemia" Blook 114, 1472-1482, 2011.
Belousov, "Sequence-specific targeting and covalent modification of human genomic DNA", Nucleic Acids Res. 5(25), 3440-3444, 1997.
Blackburn, "E. Telomerases", Annu. Rev. Biochem. 61, pp. 113-129, 1992.F.
Blommers, "Effects on the Introduction of L-Nucleotides into DNA Solution Struction of the Heterochiral Duplex d(G-C-G-(L)T-G-C-G).cntdot.d(C-G-C-A-C-G-C) Studied by NMR Spectroscopy", Biochemistry 33, 7886-7896, 1994.
Brassat, et al., "Functional p53 is required for effective execution of telomerase inhibition in BCR-ABL-positive CML cells", Experimental Hematology, 39(1), 66-76, 2011.
Brown, "Chemical synthesis and cloning of a tyrosine tRNA gene", Meth. Enzymol., 68, 109, 1979.
Brunold, C., et al., "Imetelstat, A Potent Telomerase Inhibitor, Inhibits the Spontaneous Growth of CFU-Meg In Vitro From Essential Thrombocythemia Patients but Not From Healthy Individuals", Blood (ASH Annual Meeting Abstr.), 118: Abstract 3843, 1-3, 2011.
Carobbio, et al., "Leukocytosis is a risk factor for thrombosis in essential thrombocythemia: interaction with treatment, standard risk factors, and Jak2 mutation status", Blood 109(6), 2310-2313, 2007.
Carruthers, "Chemical Synthesis and Biological Studies on Mutated Gene-control Regions", Cold Springs Harbor Symp. Quant. Biol. 47, 411-418, 1982.
Catenacci, et al., "Myelodysplasic Syndromes: A Comprehensive Review", Blood Reviews 19, 301-319, 2005.
Cazzola, et al., "Ring Sideroblasts and Sideroblastic Anemias", Haematologica, 96(6), 789-792, 2011.
Chen et al., "Secondary structure of vertebrate telomerase RNA", Cell 100, pp. 503-514, 2000.
Della Porta et al., "Myelodysplastic Syndromes with Bone Marrow Fibrosis" Haematologica, vol. 96, No. 2, 180-183, 2011.
Drummond et al., "Dysregulated Expression of the Major Telomerase Components in Leukemic Stem Cells Leukemia", vol. 19, 381-389, 2005.
El-Daly, H, et al., , "Selective Cytotoxicity and telomere damage in leukemia cells using the telomerase inhibitor BIBR1532", Blood vol. 105, No. 4, 1742-1749, 2005.
El-Kassar, et al., "Clonality Analysis of Hematopoiesis in Essential Thrombocythemia: Advantages of Studying T Lymphocytes and Platelets" Blood 89, 128-134, 1997.
Frenkel, "12-dimethylbenz[a]anthracene induces oxidative DNA modification in vivo" Free Radic. Biol. Med., 19373-19380, 1995.
Geron Corporation, Geron Corporation Reports Fourth Quarter and Annual 2012 Financial Results, Press Release, 2012.
Geron Corporation, Geron discontinues GRN1005 and Restructures to Focus on Imetelstat Development in Hematologic Malignancies and Solid Tumors with Short Telomeres, Press Release, 2012.
Geron Corporation, Geron Updates Imetelstat Development Strategy, Including Progress of Investigator-sponsored study in Myelofibrosis, Press Release, 2013.
Geron Corporation, U.S. Appl. No. 16/432,727.
Geron Corporation, Geron Press Release, Geron Presents Positive Results from Phase 2 Study of Imetelstat in Essential Thrombocythemia at the American Society of Hematology Annual Meeting, Press Release [online], Geron Corporation (retrieved on Jul. 17, 2019), Dec. 10, 2012, retrieved from the Internet URL:http://ir.geron.com/news-releases/news-release-details/geron-presents-positive-results-phase-2-study-imetelstat.
Gianelli et al., The European Consensus on Grading of Bone Marrow Fibrosis Allows a Better Prognostication of Patients with Primary Myelofibrosis, Modern Pathol., vol. 25, No. 91193-1202, 2012.
Gnatenko, et al., "Transcript profiling of human platelets using microarray and serial analysis of gene expression", Blood 101, 2285-2293, 2003.
Graubert, et al., "Recurrent Mutations in the U2AF1 Splicing Factor in Myelodysplastic Syndromes", Nat Genet., 44(1)53-57, 2012.
Gryaznov et al., "Modulation of oligonucleotide duplex and triplex stability via hydrophobic interactions Nucl. Acids Res." 21pp. 5909-5915, 1993.
Gryaznov et al., "Oligonucleotide N3'→P5' phosphoramidates as antisense agents" Nucl. Acids Res. 24(8), pp. 1508-1514, 1996.
Gryaznov et al., "Oligonucleotide N3'→P5' thiophosphoramidate telomerase template antagonists as potential anticancer agents", Nucleosides, Nucleotides & Nucl. Acids, 22(5-8), pp. 577-581, 2003.
Gryaznov et al., "RNA mimetics: oligoribonucleotide N3'-P5' phosphoramidates" Nucl. Acids Res., 26(18), pp. 4160-4171, 1998.
Gryaznov et al., "Synthesis and properties of oligonucleotides containing aminodeoxythymidine units", Nucl. Acids Res., 20(13), 3403-3491, 1992.
Gryaznov, "Oligonucleotide N3' →P5' Phosphoramidates and thiophosphoramidates as Potential Therapeutic Agents, Chemistry and Biology of Artificial Nucleic Acids", Wiley-VCH, Weinheim, Mar. 2012, ISBN 9783906390673, pp. 61-77, 2012.
Gryaznov et al., "Oligonucleotide N3'→P5' phosphoramidates as potential therapeutic agents", Biochem. Biophys. Acta 1489(1), 131-401, 1999.
Gryaznov et al., "Telomerase inhibitors—oligonucleotide phosphoramidates as potential therapeutic agents", Nucleosides, Nucleotides & Nucl. Acids, 20(4-7), 401-410, 2001.
Hanahan, et al., "Hallmarks of Cancer: The Next Generation", Cell, 144646-144674, 2011.
Harley et al., Telomerase, Checkpoints and CancerCancer Surv. 29263-29284, 1997.
Harley, "Telomere loss: Mitotic clock or genetic time bomb?" Mutation Res., 256pp. 271-282, 1991.
Hennessy et al., "New Approaches in the Treatment of Myelofibrosis", Cancer, vol. 103, No. 132-143, 2004.
Hochreiter et al., "Telomerase template antagonist GRN163L disrupts telomere maintenance, tumor growth, and metastasis of breast cancer", Clin. Cancer Res., 12(10), pp. 3184-3192, 2006.
James, et al., A unique clonal JAK2 mutation leading to constitutive signaling causes polycythaemia vera:, Nature, 434, 1144-1148, 2005.
Joseph, et al., "The Telomerase Inhibitor Imetelstat Depletes Cancer Stem Cells in Breast and Pancreatic Cancer Cell Lines", Cancer Research, 70(22), 9494-9504, 2010.
Kakiuchi et al., Inhibition of Human Tumor Cell Proliferation by the Telomerase Inhibitor TELIN, Cytologia (Tokyo), vol. 75, No. 2, 177-183, 2010.
Kelland "Overcoming the immortality of tumour cells by telomere and telomerase based cancer therapeutics", Eur. J Cancer, 41971-41979, 2005.
Keller et al., "Telomeres and telomerase in chronic myeloid leukemia: impact for pathogenesis disease progression and targeted therapy" Hematological Oncology, vol. 27, No. 3123-3129, 2009.

(56) References Cited

OTHER PUBLICATIONS

Kim et al., "A low threshold level of expression of mutant-template telomerase RNA inhibits human tumor cell proliferation", Proc. Natl. Acad. Sci. USA, 98(14), pp. 7982-7987, 2001.

Kim et al., "Telomerase Activity Is High In Essential Thrombocythemia and Polycythemia Vera, but Not In Myelofibrosis—a Comprehensive Analysis on Telomerase Activity and Cytogenetics in Myeloproliferative Neoplasm and Myelodysplastic Syndromes", Blood 116(21), abstract 4462, [online] retrieved on May 19, 2020 https://doi.org/10.1182/blood.V116.21.4462.462, 2010.

Kim, et al., "Specific association of human telomerase activity with immortal cells and cancer", Science, 266pp. 2011-2015, 1994.

Kralovics, et al., "A Gain-of-Function Mutation of JAK2 in Myeloproliferative Disorders", N. Engl. J. Med., 352, 1779-1790, 2005.

Kupihar et al., "Synthesis and application of a novel, crystalline phosphoramidite monomer with thiol terminus, suitable for the synthesis of DNA conjugates", Bioorg. Med. Chem., 9(5)pp., 1241-1247, 2001.

Lasho, et al., "SRSF2 Mutations in Primary Myelofibrosis: Significant Clustering with IDH Mutations and Independent Association with Inferior Overall and Leukemia-Free Survival" Blood, 120(20), 4168-4171, 2012.

Lebedeva et al., "Antisense oligonucleotides: promise and reality", Annu. Rev. Pharmacol. Toxicol., 41pp., 403-419, 2001.

Lee et al., "Telomere length shortening in non-Hodgkin's lymphoma patients undergoing chemotherapy", Ann. Hematol., 82pp., 492-495, 2003.

Levine, et al., "Activating mutation in the tyrosine kinase JAK2 in polycythemia vera, essential thrombocythemia, and myeloid metaplasia with myelofibrosis", Cancer Cell, 7387-7397, 2005.

Ly et al., "Functional characterization of telomerase RNA variants found in patients with hematologic disorders", Blood, vol. 105, No. 6, 2332-2339, 2005.

Macejak et al., "Adenovirus-mediated expression of a ribozyme to c-myb mRNA inhibits smooth muscle cell proliferation and neointima formation in vivo", J. Virol., 73(9), pp. 7745-7751, 1999.

Makishima, et al., "Mutations in the spliceosome machinery, a novel and ubiquitous pathway in leukemogenesis", Blood, 119(14), 3203-3210, 2012.

Maritz et al., "Targeting telomerase in Hematologic malignancy", Future Oncology, vol. 6, No. 5769-5789, 2010.

McCurdy et al., "An Improved Method for the Synthesis of N3'→P5' Phosphoramidate Oligonucleotides", Tetrahedron Lett. 38(2), pp. 207-221, 1997.

Meggendorfer, et al., "SRSF2 Mutations in 275 Cases with Chronic Myelomonocytic Leukemia (CMML)" Blood, 120(15), 3080-3088, 2012.

Mergny et al., "Natural and Phamacological Regulation of Telomerase", Nucl. Acids Res., vol. 30, No., 4, 839-865, 2002.

Mishra et al., "Improved leishmanicidal effect of phosphorotioate antisense oligonucleotides by LDL-mediated delivery", Biochem. Biophys. Acta, 1264(2), pp. 229-237, 1995.

Narang, "Improved phosphotriester method for the synthesis of gene fragments", Meth. Enzymol., 6890, 1979.

Nelson et al., "N3'-P5' oligodeoxyribonucleotide phosphoramidates: a new method of synthesis based on a phosphoramidate amine-exchange reaction", J. Org. Chem., 62pp., 7278-7287, 1997.

Nimer, "Essential Thrombocythemia: Another "Heterogeneous Disease" Better Understood?", Blood 93, 415-416, 1999.

Pallis et al., "The Telomerase Inhibitor RHPS4 Induces Telomere Shortening, DNA-Damage and Cell Death in AML Cells and Chemosensitises Cells to Daunorubicin", Blood, 114(22), 2760, 2009.

Papaemmanuil, et al., "Somatic SF3B1 Mutation in Myelodysplasia with Ring Sideroblasts", N Engl J Med. 365(15), 1384-1395, 2011.

Pascolo, E., et al., "Mechanism of human telomerase inhibition by BIBR1532, a synthetic, non-nucleosidic drug candidate", J. Biol. Chem., 277(18), pp. 15566-1557, 2002.

Pongracz et al., "Oligonucleotide N3'→P5' thiophosphoramidates: synthesis and properties", Tetrahedron Lett., 40pp., 7661-7664, 1999.

Pongracz et al., "Novel Short Oligonucleotide Conjugates as Inhibitors of Human Telomerase", Nucleosides, Nucleotides & Nucleic Acids, 22(5-8), 1627-1629, 2003.

Pruzan et al., "Allosteric inhibitors of telomerase: oligonucleotide N3'→P5' phosporamidates", Nucl. Acids Res., 30(2), pp. 559-568, 2002.

Puri et al., "Novel Therapeutics Targeting Telomerase and Telomeres", J. Cancer Sci. Ther., vol. 5, e127, 2012.

Ratain et al., "A phase I trial of GRN163L (GRN), a first-in-class telomere inhibitor, in advanced solid tumors", J. Clin. Oncol., 26p. 3581, 2008.

Roth et al., "Imetelstat (GRN163L) - telomerase-based cancer therapy", Recent Results in Cancer Research, vol. 18, 4221-4234, 2010.

Roth et al., "Shorth Telomeres and High Telomerase Activity in T-cell Prolymphocytic Leukemia" Leukemia, 21, 2456-2462, 2007.

Roth et al., "Telomerase is limiting the growth of acute myeloid leukemia cells", Leukemia, vol. 17, No. 12, 2410-2417, Dec. 2003.

Ruden et al., "Novel anticancer therapeutics targeting telomerase", Cancer Treatment Reviews, vol. 39, 444-456, 2013.

Ruella et al., "Telomere length in pH-negative chronic myeloproliferative neoplasms: it is reduced according to JAK2 V617F mutation allele burden and it is not affected by cytoreductive treatment with hydroxyurea",ASH Annual Meeting Abstracts 1161975, 2010.

Rump et al., "Preparation of conjugates of oligodeoxynucleotides and lipid structures and their interaction with low-density lipoprotein", Bioconjugate Chem., 9pp., 341-349, 1998.

Shaffer, "Geron Hit Hard by Termination of Phase II Brain Cancer Trial", Bioworld Today, vol. 23, No. 235, 1, 4, 7, Dec. 5, 2015.

Shammas et al., "Telomerase inhibitor GRN163L inhibits myeloma cell growth in vitro and in vivo", Leukemia, vol. 22, 1410, 2008.

Shay et al., "A survey of telomerase activity in human cancer" Eur. J. Cancer, 33pp., 787-791, 1997.

Shea-Herbert, et al., "Inhibition of human telomerase in immortal human cells leads to progressive telomere shortening and cell death", Proc. Natl. Acad. Sci. USA, 96(25), pp. 14276-14281, 1999.

Shea-Herbert et al., "Lipid modification of GRN163, an N3'-P5' thio-phosphoramidate oligonucleotide, enhance the potency of telomerase inhibition", Oncogene, 24pp., 5262-5268, 2005.

Shea-Herbert, et al., "Oligonucleotide N3'→P5' phosphoramidates as efficient telomerase inhibitors", Oncogene, 21pp., 638-642, 2002.

Shea et al., "Synthesis, hybridization properties and antiviral activity of lipid-oligodeoxynucleotide conjugates", Nucl. Acids Res., 18(13), pp. 3777-3783, 1990.

Silver, "Myelofibrosis: Thalidomide Finds a New Disease", Mayo Clin. Proc., vol. 79, No. 7, 857-858, 2004.

Spanoudakis et al., "Dynamics of Telomere's Length and Telomerawe Activity in Philadelphia Chromosom Negative Myeloproliferative Neoplasms", Leukemia Research, vol. 35, Issue 4, 459-464, 2011.

Sumi, M, et al., "A G-quadruplex interactive agent, telomestatin (SOT-095) induces telomere shortening with apoptosis and enhances chemosensitivity in acute myeloid leukemia", International Journal of Oncology, vol. 24, No. 6, 1481-1487, Jun. 2004.

Tauchi, T., "Activity of a Novel G-quadruplex-interactive telomerase inhibitor, SOT-095, against human leukemia cells: Involvement of ATM-dependent DNA damage response pathways", Oncogene 22(34), 5338-5347, 2003.

Tetsuzo, T, et al., "Activity of a novel G-quadruplex-interactive telomerase inhibitor, SOT-095, against human leukemia cells: Involvement of ATM-dependent DNA damage response pathways", Oncogene, vol. 22, No. (34), 5338-5347, 2003.

Theophile, K, et al., "The Expression Levels of Telomerase Catalytic Subunit hTERT and Oncogenic MYC is Essential Thrombocythemia are Affected by the Molecular Subtype", Ann Hematol., 87(4), Epub Dec. 15, 2007, 263-268, 2008.

Thol, et al., "Prognostic Significance of ASXL1 Mutations in Patients with Myelodysplastic Syndromes", J. Clin. Oncol., 29(18), 2499-2506, 2011.

(56) References Cited

OTHER PUBLICATIONS

Thompson et al., A Phase I Trial of Imetelstat in Children with Refractory or Recurrent Solid Tumors: A Children's Oncology Group Phase I Consortium Study (ADVL 1112), Clinical Cancer Research; 1-7, 2013.
Tokcaer-Keskin et al., "The Effect of Telomerase Template Antagonist GRN163L on Bone-marrow-derived Rat Mesenchymal Stem Cells is Reversible and Associated with Altered Expression", Stem Cell Reviews and Reports, vol. 6, No. 2, 1-52, 2010.
Uhlmann, E., et al., "Antisense oligonucleotides: a new therapeutic principle", Chem. Rev., 90, pp. 543-584, 1990.
US National Institutes of Health, "Imetelstat Sodium in Treating Patients with Primary or Secondary Myelofibrosis" clinicaltrials. gov NCT01731951, 2012.
US National Institutes of Health, "Open Label Study to Evaluate the Activity of Imetelstat in Patients with Essential Thrombocythemia or Polycythemia (ET/PV)", clinicaltrials.gov NCT01243073, 2010.
Van Ziffle et al., "Telomere length in subpopulations of human hematopoetic cells", Stem Cells, 21654-21660, 2003.
Wang et al., "Telomerase inhibition with an oligonucleotide telomerase template antagonist: in vitro and in vivo studies in multiple myeloma and lymphoma" Blood, 103(1), 258-266, 2004.
Ward et al., "Pharmacological telomerase inhibition can sensitize drug-resistant and drug-sensitive cells to chemotherapeutic treatment", Mol. Pharmacol., 68:3, pp. 779-786, 2005.
Wu et al., "Direct activation of TERT transcription by c-MYC", Nature Genet. 21220-224, 1999.
Wu et al., "GRN163L, a Telomerase Inhibitor for Cancer Treatment", Chinese Journal of New Drugs, vol. 19, No. 2, Fig. 1, 2010.
Yasutaka, K, et al., "Inhibition of Human Tumor Cell Proliferation by the Telomerase Inhibitor", Telincytologia, vol. 75, No. 2, 177-183, 2010.
Yoon et al., "Telomere length shortening of peripheral blood mononuclear cells in solid-cancer patients undergoing standard-dose chemotherapy might be correlated with good treatment response and neutropenia severity", Acta Haematol., 118, pp. 30-37, 2007.
Zeng, Y., et al., "MicroRNAs and small interfering RNAs can inhibit mRNA expression by similar mechanisms", Proc. Natl. Acad. Sci. USA, 100(17), pp. 9779-9784, 2003.
Ziakas, "Effect of JAK2 V617F on Thrombotic Risk in Patients with Essential Thrombocythemia: Measuring the Uncertain", Haematologica 93, 1412-1414, 2008.
Adema et al., (2013) "What lies beyond del(5q) in myelodysplastic syndrome?" Haematologica, vol. 98, No. 12, pp. 1819-1821.
Ades et al., (2014) "Myelodysplastic Syndromes." Lancet, vol. 383, No. 9936, pp. 2239-2252.
Almeida et al., (2017) "Recent Advances in the Treatment of Lower-Risk Non-del(5g) Myelodysplastic Syndromes (MDS)." Leukemia Research, vol. 52, pp. 50-57.
Baerlocher et al., (2019) "Imetelstat Inhibits Growth of Megakaryocyte Colony-forming Units From Patients with Essential Thrombocythemia." Blood Advances, vol. 3, No. 22, pp. 3724-3728.
Baerlocher et al., (2015) Supplementary Appendix, New England Journal of Medicine, vol. 373, pp. 920-928.
Beier et al., (2015) "Telomere dynamics in patients with del (5q) MDS before and under treatment with lenalidomide." Leukemia Research, vol. 39, pp. 1292-1298.
Bièche et al., (2000) "Quantitation of hTERT Gene Expression in Sporadic Breast Tumors with a Real-Time Reverse Transcription-Polymerase Chain Reaction Assay." Clin Cancer Res, vol. 6, pp. 452-459.
Blasco et al., (1997) "Telomere Shortening and Tumor Formation by Mouse Cells Lacking Telomerase RNA." Cell, vol. 91, pp. 25-34.
Briatore et al., (2009) "Increase of telomerase activity and hTERT expression in myelodysplastic syndromes." Cancer Biology and Therapy, vol. 8, No. 10, pp. 883-889.
Bruedigam et al., (2014) "Telomerase Inhibition Effectively Targets Mouse and Human AML Stem Cells and Delays Relapse Following Chemotherapy." Cell Stem Cell, vol. 15, pp. 775-790.

Cervantes, (2014) "How I treat myelofibrosis." Blood, vol. 124, No. 17, pp. 2635-2642.
Crawford et al., (2009) "Relationship between changes in hemoglobin level and quality of life during chemotherapy in anemic cancer patients receiving epoetin alfa therapy." Cancer, vol. 95, No. 4, pp. 888-895.
Dong et al., (2016) "MDS shows a higher expression of hTERT and alternative splice variants in unactivated T-cells." Oncotarget, vol. 7, No. 44, pp. 71904-71914.
Ebrahim et al., (2016) "Hematologic malignancies: new strategies to counter the BCL-2 protein." J. Cancer Res. Clin. Oncol., vol. 142, pp. 2013-2022.
European Search Report issued in European Application No. EP16197293.0 dated Apr. 5, 2017.
Fenaux et al., (2017) "Efficacy and Safety of Imetelstat in RBC Transfusion-Dependent (TD) IPSS Low/Int-1 MDS Relapsed/Refractory to Erythropoiesis-Stimulating Agents (ESA) (IMerge)." Blood, American Society of Hematology, vol. 130, 4256, 3 pages.
Fili et al., (2013) "Prospective phase II study on 5-days azacitidine for treatment of symptomatic and/or erythropoietin unresponsive patients with low/int-1-risk myelodysplastic syndromes." Clin Cancer res., vol. 19, No. 12, pp. 3297-3308.
Fischer et al., (2015) "Genomics and drug profiling of fatal TCF3-HLF-positive acute lymphoblastic leukemia identifies recurrent mutation patterns and therapeutic options." Nature Genetics, vol. 47, No. 9., 13 pages.
Garcia-Manero et al., (2011) "Hypomethylating agents and other novel strategies in myelodysplastic syndromes." J. Clin Oncol., vol. 29, No. 5, pp. 516-523.
Gissingler et al., (2016) "Impact of High Molecular Risk Mutations on Overall Survival in WHO-Defined Essential Thrombocythemia and Prefibrotic Primary Myelofibrosis." Blood, vol. 128, 1931, 4 pages.
Greenberg et al., (1997) "International scoring system for evaluating prognosis in myelodysplastic syndromes." Blood, vol. 89, No. 6, pp. 2079-2088.
Guglielmelli et al., (2014) "The number of prognostically detriment mutations and prognosis in primary myelofibrosis: an international study of 797 patients." Leukemia, vol. 28, No. 9, pp. 1804-1810.
Harley et al. (1990) "Telomeres shorten during ageing of human fibroblasts." Nature, vol. 345, pp. 458-460.
Hellstrom-Lindberg et al., (2003) "A validated decision model for treating the anaemia of myelodysplastic syndromes with erythropoietin + granulocyte colony-stimulating factor: significant effects on quality of life." British J Haematol., vol. 120, No. 6, pp. 1037-1046.
Hu, et al., (2019) Combination Treatment with Imetelstat, a Telomerase Inhibitor, and Ruxolitinib Depletes Myelofibrosis Hematopoietic Stem Cells and Progenitor Cells. Blood, vol. 134, No. 1, 963, 2 pages.
Hultdin, M, et al. (1998) Telomere analysis by fluorescence in situ hybridization and flow cytometry Nucl. Acids Res., vol. 26, No. 16, pp. 3651-3656.
International Search Report issued in PCT/US2017/044348 mailed Oct. 10, 2017.
International Search Report issued in PCT/US2018/044225 mailed Oct. 10, 2018.
Janssen Research & Development L Study to Evaluate Imetelstat (JNJ-63935937) in Subjects With International Prognostic Scoring System (IPSS) Low or Intermediate-1 Risk Myelodysplastic Syndrome (MDS) ClinicalTrials.gov Jun. 29, 2017 https://clinicaltrials.gov/ct2/history/NCT02598661?V_20=View#StudyPageTop 2017.
Jin et al., (2005) "Down Regulation of hTERT Is an Important Mechanism in Apoptosis of MUTZ-1 Cells Induced by As203" Blood, American Society of Hematology, vol. 106, No. 11, 4910.
Kelaidi et al. (2013) "Long-term outcome of anemic lower-risk myelodysplastic syndromes without 5q deletion refractory to or relapsing after erythropoiesis-stimulating agents." Leukemia, vol. 27, No. 6, pp. 1283-1290.
Kuykendall et al. (2018) "Between a rux and a hard place: evaluating salvage treatment and outcomes in myelofibrosis after ruxolitinib discontinuation." Annals of Hematology, vol. 97, pp. 435-441.

(56) References Cited

OTHER PUBLICATIONS

Langabeer et al., (2016) "Chasing down the triple-negative myeloproliferative neoplasms: Implications for molecular diagnostics." JAK-STAT, vol. 5, pp. e1248011-1-e1248011-5.

Lange et al., (2010) "Telomere Shortening and Chromosomal Instability in Myelodysplastic Syndromes." Genes, Chromosomes & Cancer, vol. 49, pp. 260-269.

Leibundgut et al., (2015) "Dynamics of Mutations in Patients with ET Treated with Imetelstat." Blood, vol. 126, No. 23, 57, 3 pages.

Loiseau et al., (2015) "New therapeutic approaches in myelodysplastic syndromes: hypomethylating agents and lenalidomide." Exp Hematol., vol. 43, No. 8, pp. 661-672.

Malcovati et al., (2006) "Predicting survival and leukemic evolution in patients with myelodysplastic syndrome." Haematologica, vol. 91, No. 12, pp. 1588-1590.

Malcovati et al., (2005) "Prognostic factors and life expectancy in myelodysplastic sydromes classified according to WHO criteria: a basis for clinical decision making." J Clin. Oncol., vol. 23, pp. 7594-7603.

Marty et al., (2016) "Calreticulin mutants in mice induce an MPL-dependent thrombocytosis with frequent progression to myelofibrosis." Blood, vol. 127, No. 10, pp. 1317-1324.

Mascarenhas et al., (2018) "Imetelstat is effective treatment for patients with intermediate-2 or high-risk myelofibrosis who have relapsed on or are refractory to Janus kinase inhibitor therapy: results of a phase 2 randomized study of two dose levels." Blood, vol. 132, No. 1, 685, 4 pages.

McNamara et al., (2019) EHA; Amsterdam, the Netherlands; Jun. 13, 2019. #PS1460.

Mesa et al., (2016) "Individualizing Care for Patients with Myeloproliferative Neoplasms: Integrating Genetics, Evolving Therapies, and Patient-Specific Disease Burden." Am Soc Clin Oncol Educ Book, vol. 35, pp. 324-335.

Mudireddy et al., (2018) "Prefibrotic versus overtly fibrotic primary myelofibrosis: clinical, cytogenetic, molecular and prognostic comparisons." Bri J. Haematol., vol. 182, pp. 594-597.

Newberry et al., (2017) "Clonal evolution and outcomes in myelofibrosis after ruxolitinib discontinuation." Blood, vol. 130, No. 9, pp. 1125-1131.

Oliva et al., (2013) "Biological activity of lenalidomide in myelodysplastic syndromes with del5q: results of gene expression profiling from a multicenter phase II study." Ann Hematol., vol. 92, No. 1, pp. 25-32.

Pardanani et al., (2014) "Definition and management of ruxolitinib treatment failure in myelofibrosis." Blood Cancer Journal, vol. 4, e268, 7 pages.

Park et al., (2017) "Outcome of lower-risk patients with myelodysplastic syndromes without 5q deletion after failure of erythropoiesis-stimulating agents." J Clin Oncol., vol. 35, No. 14, pp. 1591-1597.

Patnaik et al., (2015) "CME Information: Refractory anemia with ring sideroblasts and RARS with Thrombocytosis." Am. J. Hematol., vo. 90, No. 6, pp. 550-559.

Patnaik et al., (2017) "Refractory anemia with ring sideroblasts (RARS) and RARS with thrombocytosis (RARS-T): 2017 update on diagnosis, risk-stratification, and management." American Journal of Hematology, vol. 92, No. 3, pp. 297-310.

Prebet et al. (2017) "Outcome of patients treated for myelodysplastic syndromes without deletion 5q after failure of lenalidomide therapy." Oncotarget, vol. 8, No. 23, pp. 37866-37874.

Romero, (2015) "Haematological Cancer—Promising Results of BCL2 Inhibition." Nature Reviews Clinical Oncology, vol. 12, No. 9, 504, 1 page.

Ropio et al., (2016) "Telomerase Activation in Hematological Malignancies." Genes, vol. 7, No. 9, 13 pages.

Rufer et al., (1998) "Telomere length dynamics in human lymphocyte subpopulations measured by flow cytometry." Nature Biotechnology, vol. 16, pp. 743-747.

Rumi et al., (2014) "Clinical effect of driver mutations of JAK2, CALR, or MPL in primary myelofibrosis." Blood, vol. 124, No. 7, pp. 1062-1069.

Rusbuldt et al., (2016) "Abstract 2731: Impact of hypomethylating agents on hTERT expression and synergistic effect in combination with imetelstat, a telomerase inhibitor, in AML cell lines." Cancer Research, American Association for Cancer Research, 1-2.

Schain et al., (2019) "Survival outcomes in myelofibrosis patients treated with ruxolitinib: A population-based cohort study in Sweden and Norway." Eur J Haematol., vol. 103, pp. 614-619.

Shammo et al., (2016) "Mutations in MPNs: prognostic implications, window to biology, and impact on treatment decisions." Hematology, Am Soc Hematol Educ Program, vol. 2016, No. 1, pp. 552-560.

Shreenivas et al., (2018) Emerging drugs for the treatment of Myelofibrosis. Expert Opinion on Emerging Drugs, vol. 23, No. 1, pp. 37-49.

Sochacki et al., (2016) "Therapeutic approaches in myelofibrosis and myelodysplastic/myelolproliferative overlap syndromes." Onco. Targets Ther., vol. 9, pp. 2273-2286.

Sole et al., (2005) "Identification of novel cytogenic makers with prognostic significance in a series of 968 patients with primary myelodysplastic syndromes." Haematologica, vol. 90, No. 9, pp. 1168-1178.

Spiegel et al., (2017) "Impact of genomic alterations on outcomes in myelofibrosis patients undergoing JAK1/2 inhibitor therapy." Blood Adv., vol. 1, No. 20, pp. 1729-1738.

Steensma, (2015) "Myelodysplastic syndromes: diagnosis and treatment." Mayo Clinic Proc., vol. 90, No. 7, pp. 969-983.

Tefferi et al., (2013) "Imetelstat, a Telomerase Inhibitor, Induces Morphologic and Molecular Remissions in Myelofibrosis and Reversal of Bone Marrow Fibrosis." Blood, retrieved from the internet: URL:http://www.bloodjournal.org/content/122/21/662 [retrieved on May 26, 2017].

Tefferi et al., (2014) "Long-term survival and blast transformation in molecularly annotated essential thrombocythemia, polycythemia vera, and myelofibrosis." Blood, vol. 124, No. 16, pp. 2507-2513.

Tefferi et al., (2016) "The telomerase inhibitor imetelstat in patients (pts) with intermediate-2 or high-risk myelofibrosis (MF) previously treated with Janus kinase (JAK) inhibitor: A phase 2, randomized study." Journal of Clinical Oncology, vol. 34, Supp 15, Abstract No. TPS7079.

Terrin et al., (2007) "Telomerase expression in B-cell chronic lymphocytic leukemia predicts survival and delineates subgroups of patients with the same igVH mutation status and different outcome." Leukemia, vol. 21, pp. 965-972.

Thépot et al., (2016) "A randomized phase II trial of azacitidine +/-epetin -? in lower-risk myelodysplastic syndromes resistant to erythropoietic stimulating agents." Haematologica, vol. 101, No. 8, pp. 918-925.

Tobiasson et al., (2014) "Limited clinical efficacy of azacitidine in tranfusion-dependent, growth factor-resistant, low- and Int-1-risk MDS: Results from the nordic NMDSG08A phase II trial." Blood Cancer J., vol. 4, e189 , 7 pages.

UNC School of Medicine, History-Taking and Physical Examination, Medicine Clerkship (May 29, 2010), 3 pages, retrieved from https://www.med.unc.edu/medclerk/resources/cdim-sgim-guide/history-taking-and-physical-examinations/.

Vannucchi et al., (2013) "Mutations and prognosis in primary myelofibrosis." Leukemia, vol. 27, pp. 1861-1869.

Vasko et al., (2017) "Telomeres and Telomerase in Hematopoietic Dysfunction: Prognostic Implications and Pharmacological Interventions." Int J Mol Sci., vol. 18, No. 11., 14 pages.

Wang et al., (2014) "Atypical chronic myeloid leukemia is clinically distinct from unclassifiable myelodysplastic/myeloproliferative neoplasms." Blood, vol. 123, No. 17, pp. 2645-2651.

Wang et al., (2018) "Imetelstat, a telomerase inhibitor, is capable of depleting myelofibrosis stem and progenitor cells." Blood Adv., vol. 2, No. 18, pp. 2378-2388.

Zijlmans et al., (1997) "Telomeres in the mouse have large inter-chromosomal variations in the No. of T2AG3 repeats." Proc. Natl. Acad. Sci. USA, vol. 94, pp. 7423-7428.

Anonymous, (2016) "Abstract 2731: Impact of hypomethylating agents on hTERT expression and synergistic effect in combination with imetelstat, a telomerase inhibitor, in AML cell lines | Cancer Research | American Association for Cancer Research", pp. 1-2.

(56) References Cited

OTHER PUBLICATIONS

Drevon et al., (2018) "Myelodysplastic syndrome (MDS) with isolated trisomy 8: a type of MDS frequently associated with myeloproliferative features? A report by the Groupe Francophone des Myelodysplasies", British Journal of Haematology, 182(6):843-850.
Jafri et al., (2016) "Roles of telomeres and telomerase in cancer, and advances in telomerase-targeted therapies", Genome Medicine, 8(69):1-18.
Kishtagari et al., (2017) "Biological and clinical implications of telomere dysfunction in myeloid malignancies", Ther Adv Hematol, 8(11):317-326.
Patel et al., (2015) "Correlation of mutation profile and response in patients with myelofibrosis treated with ruxolitinib", Blood, 126(6):790-797.
Tefferi et al., (2016) "Telomerase Inhibitor Imetelstat Therapy in Refractor Anemia with Ring Sideroblasts with or without Thombocytosis", Blood Cancer Journal, 6(3):1-2.
Clinical Trials (2015) "Study to Evaluate Imetelstat (GRN163L) in Subjects With International Prognostic Scoring System (IPSS) Low or Intermediate-1 Risk Myelodysplastic Syndrome (MDS)", Geron Corporation, 20 pages, NCT ID: NCT02598661.
Paulsson and Johansson, (2006) "Trisomy 8 as the sole chromosomal aberration in acute myeloid leukemia and myelodysplastic syndromes", Science Direct, 55:37-48.
Janssen Research & Development (2016) "Study to Evaluate Imetelstat (JNJ-63935937) in Subjects with International Prognostic Scoring System (IPSS) Low or Intermediate-1 Risk Myelodysplastic Syndrome (MDS)", ClinicalTrials.gov, pp. 1-3.
Palandri et al., (2020) "Life After Ruxolitinib: Reasons for Discontinuation, Impact of Disease Phase, and Outcomes in 218 Patients with Myelofibrosis" Cancer, 126(6):1243-1252.
Santini "Treatment of low-risk myelodysplastic syndromes", Hematology Am Soc Hematol Educ Program, 1:462-469.
Smith, (2010) "The clinical and economic burden of anemia." Am J Manag Care, 16(3):S59-S66.
Tefferi et al., (2015) "Telomerase Inhibitor Imetelstat Therapy in Refractory Anemia with Ring Sideroblasts with or without Thrombocytosis", Clinical Trial, 4 pages.
Huang, (2018) "New drug research and development", Journal of International Pharmaceutical Research, 45(1):77.
The Merck Manual, (2018) 18th Edition, pp. 1098-1105.
Tefferi and Vardiman (2008) "Classification and diagnosis of myeloproliferative neoplasms: The 2008 World Health Organization criteria and point-of-care diagnostic algorithms" Leukemia, 22:14-22.

\* cited by examiner

METHODS OF TREATING MYELODYSPLASTIC SYNDROME

CROSS-REFERENCE TO RELATED APPLICATIONS

This application claims benefit of priority to U.S. Provisional Application No. 62/772,861, filed Nov. 29, 2018, U.S. Provisional Application No. 62/811,271, filed Feb. 27, 2019, and U.S. Provisional Application No. 62/860,557, filed Jun. 12, 2019, the disclosures of each of which are incorporated herein by reference in their entirety.

INTRODUCTION

Myelodysplastic syndromes (MDS) are a group of symptoms that includes cancer of the blood and bone marrow. They also include diseases such as, refractory anemia, refractory anemia with excess blasts, refractory cytopenia with multilineage dysplasia, refractory cytopenia with unilineage dysplasia, and chronic myelomonocytic leukemia. The MDS are a collection of hematological medical conditions that involve ineffective production of the myeloid class of blood cells. In MDS, the immature blood stem cells (blasts) do not become healthy red blood cells, white blood cells, or platelets. The blasts die in the bone marrow or soon after traveling to the blood leaving less room for healthy white cells, red cells, and/or platelets to form in the bone marrow.

MDS primarily affect the elderly and is characterized by anemia and other cytopenias and a high risk of leukemic transformation (Cheson et al., *Blood* 2006; 108:419-425). In clinical practice, MDS are suspected when an otherwise unexplained anemia is associated with other cytopenias, increased mean corpuscular volume, or increased red cell distribution width. Diagnosis involves bone marrow examination and cytogenetic studies. The bone marrow is typically hyperproliferative. Diagnosis is based on demonstration of erythroid, granulocyte, or megakaryocyte dysplasia in 10% or more of informative cells (Vardiman, et al., *Blood* 2009; 114(5):937-951). MDS may progress over time. For example, patients with MDS often develop severe anemia and require frequent blood transfusions. Bleeding and risk of infections also occur due to low or dysfunctional platelets and neutrophils, respectively. In some cases, the disease worsens, and the patient develops cytopenias (low blood counts) caused by progressive bone marrow failure. In other cases, the disease transforms into acute myelogenous leukemia (AML). If the overall percentage of bone marrow myeloblasts rises above a particular cutoff (20% for World Health Organization (WHO) and 30% for French-American-British (FAB) subtypes), then transformation to AML is said to have occurred. Limited treatment options exist for patients with lower risk MDS who are relapsed or refractory to erythropoiesis-stimulating agents (ESA).

The standard prognostic tool for assessing MDS is the International Prognostic Scoring System (IPSS), which classifies patients into low, intermediate-1, intermediate-2, and high-risk categories based on several prognostic variables including bone marrow blasts, cytogenetics, and presence of cytopenias. The median survival for these four groups has been estimated at 5.7, 3.5, 1.2, and 0.4 years, respectively. The median times for 25% of patients in these groups to develop AML were 9.4, 3.3, 1.1 and 0.2 years, respectively (Greenberg et al., *Blood* 1997; 89(6):2079-2088). Patients with low and intermediate-1 risk MDS may be referred to as having "lower-risk" disease, whereas those with intermediate-2 and high risk MDS may be referred to as patients with "higher-risk" disease.

In patients aged ≥70 years in Western countries, the incidence of MDS is conservatively estimated approximately at 30 to 40 cases per 100,000 population per year. Due to an aging population, the number of cases of MDS is expected to escalate. Despite the reduced rate of leukemic transformation of lower-risk patients, most patients are affected by anemia and anemia-related symptoms with profound effects on patient-reported outcomes (Almeida et al., *Leukemia Res.* 2017; 52:50-57). Many anemic patients with MDS eventually develop dependence on red blood cell ("RBC") transfusions; evidence suggests that iron overload resulting from chronic RBC transfusion may be a contributing factor in the overall morbidity of the disease (Malcovati et al., *J Clin Oncol* 2005; 23:7594-7603; Malcovati et al., *Haematologica* 2006; 91:1588-1590; Steensma D P., *Mayo Clinic Proc.* 2015; 90(7):969-983). Analysis of retrospective data from 426 patients diagnosed with MDS according to WHO criteria in Italy between 1992 and 2004 showed that a transfusion requirement of 2 units per month reduces the life expectancy of a patient with MDS by approximately 50% (Malcovati et al., *Haematologica* 2006).

The treatment strategy for MDS is largely based on the IPSS score. In patients classified as IPSS intermediate-2 or high risk (higher-risk MDS), with median survival if untreated of only about 12 months, the treatment goal is modifying the disease course, avoiding progression to AML, and extending survival. In patients classified as IPSS low or intermediate-1 risk (lower-risk MDS), survival is longer, but many patients die from causes other than MDS. Treatment of these patients mainly aims to ameliorate the consequences of cytopenias and transfusions and improve quality of life (Ades et al., *Lancet* 2014; 383(9936): 2239-2252).

For patients with lower-risk non-del(5q) MDS, first-line treatment of anemia often involves the use of erythropoiesis-stimulating agents (ESAs) or other hematopoietic growth factors. High-dose ESAs (e.g. epoetin alfa), with or without granulocyte colony-stimulating factors, have yielded erythroid response rates in the range of 30% to 50% and of median duration 2 years (id.). Key favorable prognostic factors for response to ESAs are low or absent RBC transfusion requirement (<2 packed red blood cell units/month) and low serum erythropoietin level (500 units/L) (Hellstrom-Lindberg et al., *Br J Haematol.* 2003; 120(6):1037-1046). Studies have shown that ESAs have no effect on the risk of progression to higher-risk MDS and AML, and strongly suggest that they may even improve survival in lower-risk MDS compared with RBC transfusion alone (Garcia-Manero et al., *J Clin Oncol.* 2011; 29(5):516-523). In the absence of concomitant progression to higher-risk MDS or AML, patients, who had primary refractoriness to ESA or relapsed within 6 months of response achievement, were observed to have a relatively high risk of AML transformation (23.1%) and short survival (median 3 years), whereas patients, who responded to treatment and relapsed beyond 6 months, had a more favorable outcome after failure with a 9% AML risk at 7 years and a median overall survival of 4.5 years (Kelaidi et al., *Leukemia* 2013; 27(6): 1283-1290).

There is no approved therapy in the United States for patients with lower-risk non-del(5q) MDS who are not responsive to ESA; and treatment options after ESA failure are limited. Most patients with lower-risk MDS will eventually require long-term RBC transfusion, which is often accompanied by iron overload (Ades et al., *Lancet* 2014;

Fenaux et al., *Blood* 2013; 121:4280-4286; Steensma et al., *Mayo Clinic Proc.* 2015). Life expectancy for patients with MDS has been shown to be inversely related to RBC transfusion burden (Malcovati et al., *Haematologica* 2006). Patients with chronic anemia despite frequent RBC transfusions may be at risk for associated morbidities (e.g. cardiac failure, falls, fatigue) and lower quality of life (Crawford et al., *Cancer* 2002; 95:888-895).

Hypomethylating agents (HMA) (e.g. azacitidine and decitabine) have been approved as treatments for all French-American-British (FAB) subtypes, which includes some lower-risk MDS patients. While these drugs reduce transfusion requirements in higher-risk MDS patients, evidence for improvement of long-term outcomes for lower-risk patients who receive HMAs after ESA failure is absent. In a retrospective study of 1,698 patients with non-del(5q) lower-risk MDS treated with ESAs, patients receiving subsequent treatment with HMAs (n=194) after ESA failure did not experience significant improvement in 5-year overall survival (Park et al., *J Clin Oncol.* 2017; 35(14):1591-1597). According to other reports, in cohorts of patients with lower-risk MDS who are transfusion dependent after ESA failure, azacitidine induces RBC-TI in approximately 14% to 33% of patients (Fili et al., *Clin Cancer Res.* 2013; 19:3297-3308; Thepot et al., *Haematologica.* 2016; 101: 918-925; Tobiasson et al., *Blood Cancer J.* 2014: 4, e189). In view of the limited benefit and observed toxicities (neutropenia, infection), azacitidine cannot be recommended as treatment for these patients (Tobiasson et al., *Blood Cancer J.* 2014).

The del(5q) chromosomal abnormality is observed in 10% to 15% of patients with MDS and is associated with a favorable prognosis (Oliva et al., *Ann Hematol.* 2013; 92(1): 25-32). Treatment with lenalidomide results in transfusion independence for approximately two-thirds of such patients (Ades et al., *Lancet* 2014; Fenaux et al., *Blood* 2013; 121(21):4280-4286). In a Phase 3 study, median duration of TI was not reached (median follow-up, 1.55 years) (Fenaux et al., *Blood* 2011; 118(14):3765-3776). Myelosuppression was the most frequently reported Grade 3 or 4 toxicity, and close monitoring of blood counts is required in the first weeks of lenalidomide therapy (id.).

Lenalidomide has also been studied as a treatment for transfusion-dependent non-del(5q) MDS, which represent 85% to 90% of the MDS population. The majority of these subjects do not respond to lenalidomide. Hematologic toxicity (i.e., neutropenia, and thrombocytopenia) was milder than in patients with del(5q) MDS (Loiseau et al., *Exp Hematol.* 2015; 43(8):661-72). Like HMAs, treatment with lenalidomide following ESA failure has not been shown to significantly improve overall survival when used to treat lower-risk non-del(5q) MDS patients (Park et al., *J Clin Oncol.* 2017).

While immunosuppressive therapy is a treatment option for certain lower-risk non-del(5q) patients, no significant effect on transformation-free survival was observed; and adverse events, including hematologic toxicity and associated severe adverse events, such as hemorrhage and infections, have been reported (Almeida et al., *Leukemia Res.* 2017). Allogeneic stem cell transplantation is typically reserved for medically fit higher-risk MDS patients, but may be considered an option for select lower-risk patients, such as those aged <60 to 70 years with IPSS intermediate-1-risk MDS, poor-risk cytogenetics, or persistent blast elevation, if alternative therapeutic options are ineffective (id.).

SUMMARY

Methods of monitoring therapeutic efficacy in a subject with MDS are provided. Also provided is a method of identifying a subject with myelodysplastic syndrome (MDS) for treatment with a telomerase inhibitor, and methods of treating MDS. The subject methods can include administering to the subject an effective amount of a telomerase inhibitor and assessing the hTERT expression levels in a biological sample obtained from the subject. In some cases, a 50% or greater reduction in hTERT expression level identifies a subject who has an increased likelihood of benefiting from treatment with the telomerase inhibitor. The subject can be naive to treatment with a HMA, lenalidomide, or both. In some cases, the subject is classified as having low or intermediate-1 IPSS risk MDS and/or MDS relapsed/refractory to Erythropoiesis-Stimulating Agent (ESA). In certain cases, the subject is non-del5q. In some instances, the telomerase inhibitor is imetelstat or imetelstat sodium.

Methods of treating MDS in a subject with a telomerase inhibitor are provided. The telomerase inhibitor is imetelstat or imetelstat sodium. The subject can be naive to treatment with a HMA, lenalidomide, or both. In some cases, the subject is classified as having low or intermediate-1 IPSS risk MDS and/or MDS relapsed/refractory to Erythropoiesis-Stimulating Agent (ESA). In certain cases, the subject is non-del5q. In some cases, the subject is classified as IPSS-R intermediate and poor cytogenetic risk.

BRIEF DESCRIPTION OF THE DRAWINGS

The foregoing summary, as well as the following detailed description of the invention, will be better understood when read in conjunction with the appended figures. For the purpose of illustrating the invention, the figures demonstrate embodiments of the present invention. It should be understood, however, that the invention is not limited to the precise arrangements, examples, and instrumentalities shown.

DETAILED DESCRIPTION

Figure 1A:
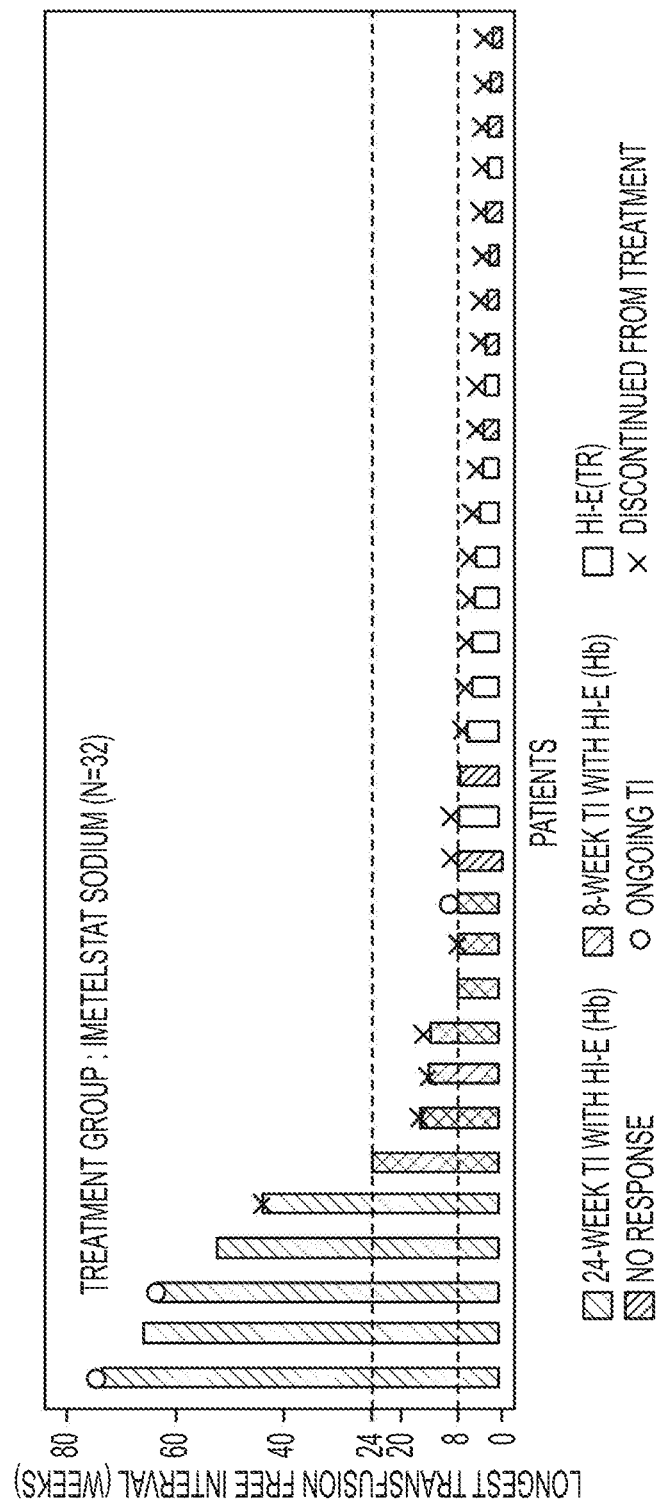
FIGS. 1A and 1B (first data cut) show waterfall plots of the longest transfusion-free interval (FIG. 1A) and absolute change in transfusion amount in the best 8-week interval (FIG. 1B) in a study of imetelstat sodium in red blood cell (RBC) transfusion-dependent (TD) patients as described herein in the experimental section. HI-E=hematologic improvement-erythroid based on a Hb rise of at least 1.5 g/dL above the pretreatment level for at least 8 weeks or reduction of at least 4 units of RBC transfusions/8 weeks compared with the prior RBC transfusion burden (criterion adapted from IWG 2006); HI-E Hb=HI-E with sustained rise in hemoglobin by at least 1.5 g/dL over 8 weeks; TI=transfusion independence; TR=transfusion reduction by at least 4 units over 8 weeks.

This application provides for methods of monitoring therapeutic efficacy in a subject with MDS. Also provided is a method of identifying a subject with myelodysplastic syndrome (MDS) for treatment with a telomerase inhibitor, and methods of treating MDS. The subject methods can include administering to the subject an effective amount of a telomerase inhibitor and assessing the hTERT expression levels in a biological sample obtained from the subject. In some cases, a 50% or greater reduction in hTERT expression level identifies a subject who has an increased likelihood of benefiting from treatment with the telomerase inhibitor. The subject can be naive to treatment with a HMA, lenalidomide, or both. In some cases, the subject treated is classified as having: low IPSS risk MDS, intermediate-1 IPSS risk MDS, MDS relapsed to Erythropoiesis-Stimulating Agent (ESA), MDS refractory to MS, or combination thereof. The subject may also be non-del5q. For clarity of disclosure, and not by way of limitation, the detailed description of the invention is divided into subsections that describe or illustrate certain features, embodiments, or applications of the present invention. In some embodiments, the subject is diagnosed as having trisomy 8.

A. Definitions

As used herein, the term "about" when referring to a measurable value such as an amount, a temporal duration, and the like, is meant to encompass variations of between ±20% and ±0.1%, preferably ±20% or ±10%, more preferably ±5%, even more preferably ±1%, and still more preferably ±0.1% from the specified value, as such variations are appropriate to perform the disclosed methods.

The term "pharmaceutically acceptable salt" means a salt which is acceptable for administration to a patient, such as a mammal (salts with counterions having acceptable mammalian safety for a given dosage regime). Such salts can be derived from pharmaceutically acceptable inorganic or organic bases and from pharmaceutically acceptable inorganic or organic acids. "Pharmaceutically acceptable salt" refers to pharmaceutically acceptable salts of a compound, which salts are derived from a variety of organic and inorganic counter ions well known in the art and include, by way of example only, sodium, and the like; and when the molecule contains a basic functionality, salts of organic or inorganic acids, such as hydrochloride, and the like. Pharmaceutically acceptable salts of interest include, but are not limited to, aluminum, ammonium, arginine, barium, benzathine, calcium, cholinate, ethylenediamine, lysine, lithium, magnesium, meglumine, procaine, potassium, sodium, tromethamine, N-methylglucamine, N,N'-dibenzylethylenediamine, chloroprocaine, diethanolamine, ethanolamine, piperazine, zinc, diisopropylamine, diisopropylethylamine, triethylamine and triethanolamine salts.

The term "salt(s) thereof" means a compound formed when a proton of an acid is replaced by a cation, such as a metal cation or an organic cation and the like. Preferably, the salt is a pharmaceutically acceptable salt. By way of example, salts of the present compounds include those wherein the compound is protonated by an inorganic or organic acid to form a cation, with the conjugate base of the inorganic or organic acid as the anionic component of the salt. Salts of interest include, but are not limited to, aluminum, ammonium, arginine, barium, benzathine, calcium, cesium, cholinate, ethylenediamine, lithium, magnesium, meglumine, procaine, N-methylglucamine, piperazine, potassium, sodium, tromethamine, zinc, N,N'-dibenzylethylene-diamine, chloroprocaine, diethanolamine, ethanolamine, piperazine, diisopropylamine, diisopropylethylamine, triethylamine and triethanolamine salts. It is understood that for any of the oligonucleotide structures depicted herein that include a backbone of internucleoside linkages, such oligonucleotides may also include any convenient salt forms. In some embodiments, acidic forms of the internucleoside linkages are depicted for simplicity. In some instances, the salt of the subject compound is a monovalent cation salt. In certain instances, the salt of the subject compound is a divalent cation salt. In some instances, the salt of the subject compound is a trivalent cation salt. "Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. When the solvent is water, the solvate formed is a hydrate.

"Stereoisomer" and "stereoisomers" refer to compounds that have same atomic connectivity but different atomic arrangement in space. Stereoisomers include for example cis-trans isomers, E and Z isomers, enantiomers, and diastereomers. As to any of the groups disclosed herein which contain one or more substituents, it is understood, of course, that such groups do not contain any substitution or substitution patterns which are sterically impractical and/or synthetically non-feasible. All stereoisomers are intended to be included within the scope of the present disclosure.

A person of ordinary skill in the art would recognize that other tautomeric arrangements of the groups described herein are possible. It is understood that all tautomeric forms of a subject compound are encompassed by a structure where one possible tautomeric arrangement of the groups of the compound is described, even if not specifically indicated.

It is intended to include a solvate of a pharmaceutically acceptable salt of a tautomer of a stereoisomer of a subject compound. These are intended to be included within the scope of the present disclosure.

Before certain embodiments are described in greater detail, it is to be understood that this invention is not limited to certain embodiments described, as such may, of course, vary. It is also to be understood that the terminology used herein is for the purpose of describing certain embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods, and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates, which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

As used throughout, "MDS" refers to myelodysplastic syndrome or myelodysplastic syndromes.

B. Pharmacodynamics (PD)

The present disclosure is based in part on a pharmacodynamic effect demonstrating an association between response to telomerase inhibition therapy in subjects with a MDS and a decrease in telomerase hTERT expression levels in the subjects from baseline levels. For example, in the clinical study described herein, a higher % of subjects achieved a 50% or more decrease in hTERT RNA expression levels in 8-week transfusion independent (TI) responders than in non-responders.

The present disclosure provides for stratification and identification or selection of patients likely to benefit from telomerase inhibition therapy for MDS, and provides methods of monitoring response, relapse, and prognosis in subjects undergoing treatment.

Aspects of the present disclosure include methods of identifying or selecting subjects with myelodysplastic syndrome (MDS) for treatment with a telomerase inhibitor, and methods of treating MDS. Methods of monitoring therapeutic efficacy in a subject with MDS are also provided. In some case, the pharmacodynamic effect on which an embodiment of the subject methods is based is reduction of hTERT RNA expression by 50% or more, such as 60% or more, 70% or more, 80% or more, or 90% or more.

The telomerase ribonucleoprotein consists of components or subunits, two of these being telomerase RNA template (hTR), and telomerase reverse transcriptase protein (hTERT). hTERT expression levels can be assessed, determined and/or measured using any convenient methods. A variety of methods can be applied for the amplification, detection and measurement of mRNA of telomerase components or related proteins in bodily fluids. Methods and assays of interest which may be adapted for use in the subject methods include, but are not limited to, real-time quantitative RT-PCR assays, e.g., based on based on TaqMan fluorescence methodology, immunohistochemistry methods for protein expression, and methods described by U.S. Pat. No. 6,607,898, Bieche et al., Clin. Cancer Res Feb. 1 2000 (6) (2) 452-459, Terrin et al. ("Telomerase expression in B-cell chronic lymphocytic leukemia predicts survival and delineates subgroups of patients with the same igVH mutation status and different outcome." Leukemia 2007; 21: 965-972), and Palma et al. ("Telomere length and expression of human telomerase reverse transcriptase splice variants in chronic lymphocytic leukemia." Experimental Hematology 2013; 41: 615-626).

The hTERT expression levels can be assessed or measured in any convenient target cells. Target cells can be any convenient cells of the patient, including but not limited to, cells of the bone marrow or peripheral blood of the patient. In some cases, the target cells are isolated from a bone marrow sample of the patient. In some cases, the target cells are isolated from a peripheral blood sample of the patient. The target cells can be granulocytes.

hTERT RNA expression levels can be assessed or measured in a RNA sample using any convenient methods. A RNA sample may be obtained by first obtaining a bone marrow sample, a peripheral blood sample, or both and then isolating the RNA from the bone marrow sample, the peripheral blood sample, or both. In one embodiment, the step of obtaining a sample from a patient comprises: obtaining a bone marrow sample from the patient, isolating cells from the bone marrow sample, and extracting RNA and/or DNA from the isolated cells. In another embodiment, the step of obtaining a RNA sample from a patient comprises: obtaining a peripheral blood sample from the patient; isolating cells from the peripheral blood sample (e.g. granulocytes); and extracting RNA and/or DNA from the isolated cells.

C. Treatment

Aspects of the present disclosure include methods of treating a myelodysplastic syndrome (MDS) with a telomerase inhibitor in a subject that is naive to treatment with particular agents, e.g., an agent selected from a hypomethylating agent (HMA) and lenalidomide. A subject is considered to be treatment "naive" if the subject has never undergone the particular treatment for an illness. Treatment of patients with MDS relapsed/refractory to an ESA therapy with imetelstat can improve outcomes, including lower incidence of anemia.

A subject is a mammal in need of treatment for cancer. Generally, the subject is a human patient. In some embodiments of the invention, the subject can be a non-human mammal such as a non-human primate, an animal model (e.g., animals such as mice and rats used in screening, characterization, and evaluation of medicaments) and other mammals. As used herein, the terms patient, subject and individual are used interchangeably.

As used herein, and as well-understood in the art, "treatment" is an approach for obtaining beneficial or desired results, including clinical results. For purposes of this invention, beneficial or desired clinical results include, but are not limited to, alleviation or amelioration of one or more symptoms, diminishment of extent of disease, stabilized (i.e., not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

In certain instances, the subject method provides an enhanced therapeutic response in those subjects who have not previously been treated with a hypomethylating agent (HMA) or lenalidomide, relative to subjects who were so treated previously. By "enhanced therapeutic response" is meant a statistically significant improvement in a primary and/or secondary endpoint of MDS therapy and/or amelioration of one or more symptoms of MDS (e.g., as described herein), e.g., rate and/or duration of red blood cell (RBC) transfusion-independence (TI), or hematologic improvement (HI) rate relative to an appropriate control. In some cases, the subject methods provide a therapeutic effect of red blood cell (RBC) transfusion-independence (TI), e.g., lasting 4 weeks or longer, such as 5 weeks or longer, 6 weeks or longer, 7 weeks or longer, 8 weeks or longer, 9 weeks or longer, 10 weeks or longer, 12 weeks or longer, 16 weeks or longer, 20 weeks or longer, 24 weeks or even longer. In some instances, time to TI and/or duration of TI is significantly improved. In certain instances, the subject method provides a duration of TI that is 24 weeks or longer, such as 30 weeks or longer, 36 weeks or longer, 42 weeks or longer, 48 weeks or longer, 60 weeks or longer, or even longer.

A hypomethylating agent (HMA) is an agent that inhibits DNA methylation, e.g., by blocking the activity of DNA methyltransferase (DNA methyltransferase inhibitors/DNMT inhibitors). HMAs of interest include, but are not limited to, decitabine (CAS Registry Number: 2353-33-5; 5-aza-2'-deoxycytidine), azacitidine (CAS Registry Number: 320-67-2, 5-azacytidine) and guadecitabine (SGI-110). In some instances, the subject is treatment naive to decitabine. In some instances, the subject is treatment naive to azacitidine. In other instances, the subject is treatment naive to both decitabine and azacitidine.

Lenalidomide is a drug that is used to treat a variety of inflammatory disorders and cancers, including multiple myeloma and MDS. Lenalidomide (CAS Registry Number: 191732-72-6; 2,6-Piperidinedione, 3-(4-amino-1,3-dihydro-1-oxo-2H-isoindol-2-yl)-); 3-(4-Amino-1-oxoisoindolin-2-yl)piperidine-2,6-dione) is a derivative of thalidomide. Lenalidomide has various mechanisms of action that provide a broad range of biological activities that can be exploited to treat a variety of hematologic and solid cancers.

Deletion 5q (del5q) refers a chromosomal abnormality found in particular forms of MDS subjects (Adema et al., *Haematologica*. 2013 December; 98(12): 1819-1821; Sole et al., *Haematologica*. 2005; 90(9): 1168-78). In some cases of the subject methods, the subject is a human patient who has del5q. In some cases, the subject is a human patient who is non-del5q. A non-del5q subject is a subject that does not have the del5q chromosomal abnormality. In certain cases, the non-del5q subject is human.

In certain instances, the subject has not received prior treatment with either a hypomethylating agent (HMA) or lenalidomide and does not have a del(5q) chromosomal abnormality (e.g., is non-del5q). In certain cases, the non-del5q subject is human.

In certain embodiments, the subject is a human patient with intermediate or poor cytogenetic risk. In some instances, the subject is a human patient diagnosed as having trisomy 8. In certain instances, the subject is a human patient with trisomy 8 mosaicism. In other instances, the subject is a human patient with trisomy 8 without mosaicism. The term "mosaicism" is used herein in its conventional sense to refer to a condition in which cells within the subject have different genetic makeup. In human patients diagnosed as having trisomy 8 with mosaicism, some of the subject's cells have three copies of chromosome 8 while other cells have two copies of chromosome 8.

In certain embodiments, methods include identifying a subject with myelodysplastic syndrome (MDS) for treatment with a telomerase inhibitor, where the method includes: identifying a subject as having trisomy 8 (with or without mosaicism); measuring hTERT expression level in a biological sample obtained from the patient after administration of a telomerase inhibitor; and comparing the hTERT expression level in the biological sample to a baseline hTERT expression level prior to administration of the telomerase inhibitor; wherein a reduction in hTERT expression level in the biological sample identifies a patient who has an increased likelihood of benefiting from treatment with the telomerase inhibitor.

In other embodiments, methods include treating myelodysplastic syndrome (MDS) in a subject diagnosed as having trisomy 8, where the method includes: identifying a subject diagnosed as having trisomy 8; administering to the subject an effective amount of a telomerase inhibitor; and assessing hTERT expression level in a biological sample obtained from the patient after administration of the telomerase inhibitor.

In yet other embodiments, methods include monitoring therapeutic efficacy in a subject with myelodysplastic syndrome (MDS), where the method includes: measuring hTERT expression level in a biological sample obtained from a patient diagnosed as having trisomy 8 after administration of a telomerase inhibitor; and comparing the hTERT expression level in the biological sample to a baseline hTERT expression level prior to administration of the telomerase inhibitor; wherein a 50% or greater reduction in hTERT expression level in the biological sample identifies a subject who has an increased likelihood of benefiting from treatment with the telomerase inhibitor.

In methods according to certain embodiments, the subject is a patient diagnosed as having trisomy 8. In other embodiments, the subject is a patient diagnosed as having trisomy 8 and is naïve to treatment with an agent selected from a hypomethylating agent (HMA), lenalidomide, and combination thereof. In other embodiments, the subject is a patient diagnosed as having trisomy 8 and is a non-del5q human patient. In still other embodiments, the subject is a patient diagnosed as having trisomy 8 and the MDS is relapsed or refractory MDS, such as MDS relapsed/refractory to erythropoiesis-stimulating agent (ESA).

D. Myelodysplastic Syndrome (MDS)

Myelodysplastic syndrome ("MDS") is a group of diseases that includes cancers of the blood and bone marrow, which in some cases can be characterized by cytopenias resulting from ineffective hemopoiesis. A variety of MDS can be treated using the subject methods, including but are not limited to, diseases such as refractory anemia, refractory anemia with excess blasts, refractory cytopenia with multilineage dysplasia, refractory cytopenia with unilineage dysplasia, chronic myelomonocytic leukemia, MDS with isolated del (5q) and MDS unclassifiable.

MDS is characterized by clonal myeloproliferation arising from malignant progenitor cell clones that have shorter telomeres and multiple clonal genetic abnormalities. Telomerase activity (TA) and expression of human telomerase reverse transcriptase (hTERT) is significantly increased in MDS and may play a role in dysregulated cell growth, leading to continued and uncontrolled proliferation of malignant progenitor cell clones. Higher TA and hTERT as well as shorter telomere length are poor prognostic features for patients with low-risk MDS, leading to shorter overall survival. There are limited treatment options for anemia in lower-risk MDS that has relapsed after or is refractory to ESA therapy. Targeting MDS clones with imetelstat can improve outcomes, including anemia, in patients with MDS relapsed/refractory to an ESA therapy.

In some embodiments, the subject methods find use in alleviating at least one symptom associated with myelodysplastic syndrome, such as, e.g., refractory anemia, refractory anemia with excess blasts, refractory cytopenia with multilineage dysplasia, refractory cytopenia with unilineage dysplasia, and chronic myelomonocytic leukemia. In some embodiments, the symptoms include shortness of breath, fatigue, weakness, fainting, nosebleeds, bruising, bleeding from mouth or gums, bloody stool, petechiae, or stroke.

In some instances, the subject has a relapsed or refractory MDS. "Refractory MDS" refers to patients who still have MDS cells in their bone marrow after treatment with any convenient MDS-related therapy. "Relapsed MDS" refers to patients who have a return of MDS cells in their bone marrow and a decrease in normal blood cells after remission.

In certain instances, the subject has MDS relapsed/refractory to Erythropoiesis-Stimulating Agent (ESA). ESAs can increase hemoglobin levels and abolish transfusion dependence for a period of time in some MDS cases. ESAs of interest include but are not limited to erythropoietin-alpha, erythropoietin-beta, and darbepoetin.

In some embodiments, the subject is identified as a human patient having trisomy 8. In certain instances, the subject is a human patient with trisomy 8 mosaicism. In other instances, the subject is a human patient with trisomy 8 without mosaicism.

In certain embodiments of the subject method, the subject is classified as a low or intermediate-1 IPSS risk MDS subject. Myelodysplastic syndromes (MDS) patients can divided into lower-risk groups (low and intermediate-1 [INT-1] IPSS), in which apoptotic events in the marrow are prevalent and there is a defective response to cytokines (including erythropoietin), and higher-risk groups (intermediate-2 [INT-2] and high IPSS), in which a block in the maturation of marrow progenitors is the principal alteration. In some cases, transfusion dependence is a negative prognostic variable. As such, in certain embodiments of the method, the subject is Red Blood Cell (RBC) transfusion dependent. In some cases, the transfusion-dependent subject has a RBC transfusion requirement of about 4 units or more over 8 weeks; or from 4-14 units over an 8-week period, or about 6 units or more per 8 weeks prior to administration according to the subject method. A unit of packed red blood cells (PRBCs) can be about 300 mL/unit. A unit of Whole blood can be about 450-500 mL/unit.

The International Prognostic Scoring System (IPSS) is a system developed for staging MDS. The IPSS rates 3 factors: the percentage of leukemic blast cells in the bone marrow cells (scored on a scale from zero to 2); chromosome abnormalities, if any, in the marrow cells (scored from zero to 1); and the presence of one or more low blood cell counts (scored as zero or 0.5). Each factor is given a score, with the lowest scores having the best outlook. Then the scores for the factors are added together to make the IPSS score. The IPSS puts people with MDS into 4 groups: low risk; intermediate—1 risk; intermediate—2 risk; and high risk.

E. Telomerase Inhibitors

Any convenient telomerase inhibitors can find use in the subject methods. In some embodiments, the telomerase inhibitor is an oligonucleotide with telomerase inhibiting activity, in particular an oligonucleotide as defined in WO 2005/023994 and/or WO 2014/088785, the disclosures of which are herein incorporated by reference in their entirety. In some cases, one or more than one telomerase inhibitor (e.g., two or three telomerase inhibitors) can be administered to a mammal to treat a hematological malignancy.

Imetelstat

In certain embodiments, the telomerase inhibitor is imetelstat, including tautomers thereof and salts thereof, e.g., pharmaceutically acceptable salts. Imetelstat is a novel, first-in-class telomerase inhibitor with clinical activity in hematologic malignancies (Baerlocher et al., NEJM 2015; 373:920-928; Tefferi et al., NEJM 2015; 373:908-919) (shown below):

(SEQ ID NO: 1)

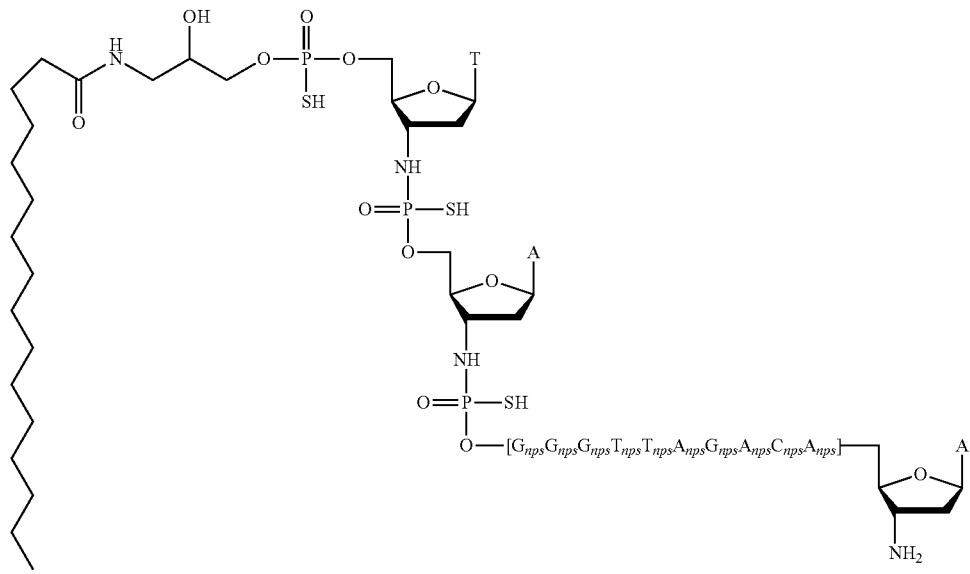

where "nps" represents a thiophosphoramidate linkage-NH—P(=O)(SH)-O-, connecting the 3'-carbon of one nucleoside to the 5'-carbon of the adjacent nucleoside.

In certain instances, the telomerase inhibitor is imetelstat sodium including tautomers thereof. Imetelstat sodium is the sodium salt of imetelstat, which is a synthetic lipid-conjugated, 13-mer oligonucleotide N3'→P5'-thio-phosphoramidate. Imetelstat sodium is a telomerase inhibitor that is a covalently-lipidated 13-mer oligonucleotide (shown below) complimentary to the human telomerase RNA (hTR) template region. The chemical name for imetelstat sodium is: DNA, d(3'-amino-3'-deoxy-P-thio) (T-A-G-G-G-T-T-A-G-A-C-A-A), 5'-[O-[2-hydroxy-3-(hexadecanoylamino)propyl] phosphorothioate], sodium salt (1:13) (SEQ ID NO: 1). Imetelstat sodium does not function through an anti-sense mechanism and therefore lacks the side effects commonly observed with such therapies.

(SEQ ID NO: 1)

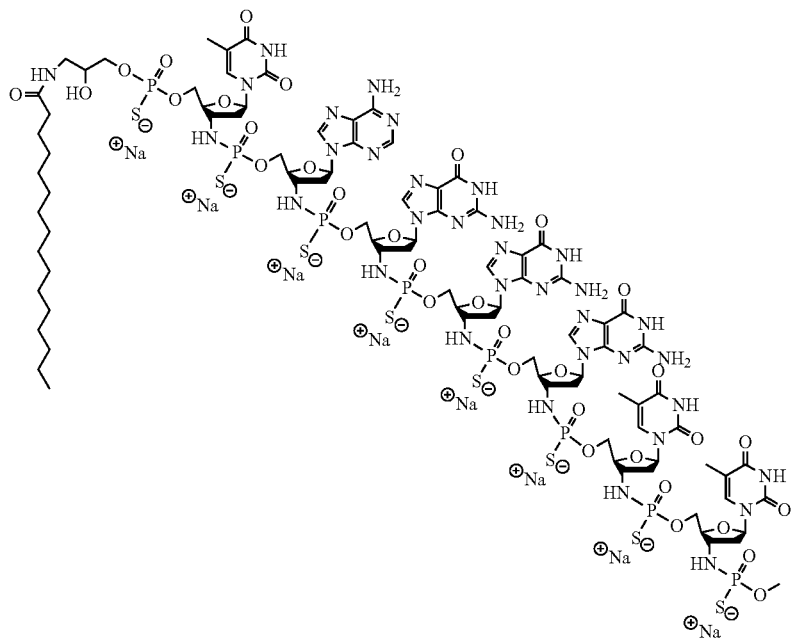

-continued

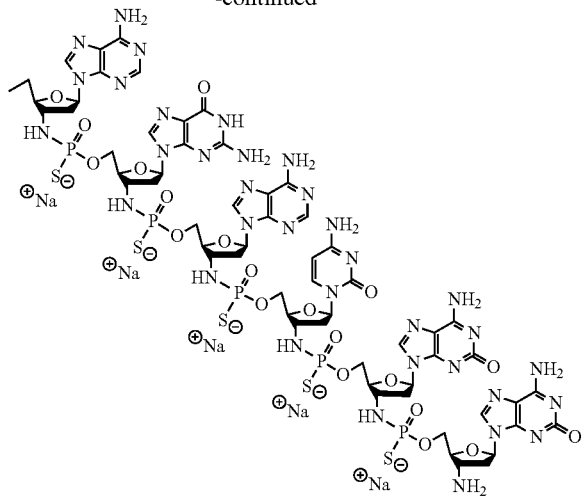

Imetelstat sodium

Unless otherwise indicated or clear from the context, references herein to imetelstat also include tautomers thereof and salts thereof, e.g., pharmaceutically acceptable salts. As mentioned, imetelstat sodium in particular is the sodium salt of imetelstat. Unless otherwise indicated or clear from the context, references herein to imetelstat sodium also include all tautomers thereof.

Imetelstat and imetelstat sodium can be produced, formulated, or obtained as described elsewhere (see e.g. Asai et al., *Cancer Res.*, 63:3931-3939 (2003), Herbert et al., *Oncogene*, 24:5262-5268 (2005), and Gryaznov, *Chem. Biodivers.*, 7:477-493 (2010)). Unless otherwise indicated or clear from the context, references herein to imetelstat also include salts thereof. As mentioned, imetelstat sodium in particular is the sodium salt of imetelstat.

Imetelstat targets the RNA template of telomerase and inhibits telomerase activity and cell proliferation in various cancer cell lines and tumor xenografts in mice. Phase 1 studies involving patients with breast cancer, non-small-cell lung cancer and other solid tumors, multiple myeloma, or chronic lymphocytic leukemia have provided information on drug pharmacokinetics and pharmacodynamics. A subsequent phase 2 study involving patients with essential thrombocythemia showed platelet-lowering activity accompanied by a significant reduction in JAK2 V617F and CALR mutant allele burdens. Imetelstat sodium is routinely administered intravenously; it is contemplated that in the practice of the subject methods other administration routes also can be used, such as intrathecal administration, intratumoral injection, oral administration and others. Imetelstat sodium can be administered at doses comparable to those routinely utilized clinically. In certain embodiments, imetelstat sodium is administered as described elsewhere herein.

A particular embodiment is according to any one of the other embodiments, wherein imetelstat is limited to imetelstat sodium.

F. Pharmaceutical Compositions

For ease of administration, the telomerase inhibitor (e.g., as described herein) may be formulated into various pharmaceutical forms for administration purposes. In some cases, the telomerase inhibitor is administered as a pharmaceutical composition. The carrier or diluent of the pharmaceutical composition must be "acceptable" in the sense of being compatible with the other ingredients of the composition and not deleterious to the recipients thereof. The pharmaceutical composition may be in unitary dosage form suitable, in particular, for administration orally, rectally, percutaneously, by parenteral injection or by inhalation. In some cases, administration can be via intravenous injection. For example, in preparing the composition in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules and tablets. Because of their ease in administration, tablets and capsules represent the most advantageous oral dosage unit forms in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable solutions, for example, may be prepared in which the carrier comprises saline solution, glucose solution or a mixture of saline and glucose solution. Injectable solutions containing the telomerase inhibitor described herein may be formulated in oil for prolonged action. Appropriate oils for this purpose are, for example, peanut oil, sesame oil, cottonseed oil, corn oil, soybean oil, synthetic glycerol esters of long chain fatty acids and mixtures of these and other oils. Injectable suspensions may also be prepared in which case appropriate liquid carriers, suspending agents and the like may be employed. Also included are solid form preparations that are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired composition. The composition may be administered in various ways, e.g., as a transdermal patch, as a spot-on, as an ointment.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

In order to enhance the solubility and/or the stability of the drug described herein in pharmaceutical compositions, it can be advantageous to employ α-, β- or γ-cyclodextrins or their derivatives, in particular hydroxyalkyl substituted cyclodextrins, e.g. 2 hydroxypropyl-β-cyclodextrin or sulfobutyl-β-cyclodextrin. Also, co-solvents such as alcohols may improve the solubility and/or the stability of the telomerase inhibitor in pharmaceutical compositions.

Depending on the mode of administration, the pharmaceutical composition will preferably comprise from 0.05 to 99% by weight, more preferably from 0.1 to 70% by weight, even more preferably from 0.1 to 50% by weight of the telomerase inhibitor described herein, and from 1 to 99.95% by weight, more preferably from 30 to 99.9% by weight, even more preferably from 50 to 99.9% by weight of a pharmaceutically acceptable carrier, all percentages being based on the total weight of the composition.

G. Administration and Administration Regimens

The frequency of administration can be any frequency that reduces the severity of a symptom of a MDS (e.g., as described herein) without producing significant toxicity to the subject. For example, the frequency of administration can be from about once every two months to about once a week, alternatively from about once a month to about twice a month, alternatively about once every six weeks, about once every 5 weeks, alternatively about once every 4 weeks, alternatively about once every 3 weeks, alternatively about once every 2 weeks or alternatively about once a week. The frequency of administration can remain constant or can be variable during the duration of treatment. A course of treatment with a composition containing one or more telomerase inhibitors can include rest periods. For example, a composition containing a telomerase inhibitor can be administered weekly over a three-week period followed by a two-week rest period, and such a regimen can be repeated multiple times. As with the effective amount, various factors can influence the actual frequency of administration used for a particular application. For example, the effective amount, duration of treatment, use of multiple treatment agents, route of administration, and severity of the MDS and related symptoms may require an increase or decrease in administration frequency.

An effective duration for administering a composition containing a telomerase inhibitor (e.g., imetelstat or imetelstat sodium) can be any duration that reduces the severity of a symptom of a MDS (e.g., as described herein) without producing significant toxicity to the subject. Thus, the effective duration can vary from one month to several months or years (e.g., one month to two years, one month to one year, three months to two years, three months to ten months, or three months to 18 months). In general, the effective duration for the treatment of a MDS can range in duration from two months to twenty months. In some cases, an effective duration can be for as long as an individual subject is alive. Multiple factors can influence the actual effective duration used for a particular treatment. For example, an effective duration can vary with the frequency of administration, effective amount, use of multiple treatment agents, route of administration, and severity of the MDS and related symptoms.

In certain instances, a course of treatment and the severity of one or more symptoms related to a MDS can be monitored. Any method can be used to determine whether or not the severity of a symptom of a MDS is reduced. For example, the severity of a symptom of a MDS (e.g., as described herein) can be assessed using biopsy techniques.

Telomerase inhibitors as used in the subject methods can be administered at any dose that is therapeutically effective, such as doses comparable to those routinely utilized clinically. Specific dose regimens for known and approved anti-cancer agents (e.g., the recommended effective dose) are known to physicians and are given, for example, in the product descriptions found in the PHYSICIANS' DESK REFERENCE, 2003, 57th Ed., Medical Economics Company, Inc., Oradell, N.J.; Goodman & Gilman's THE PHARMACOLOGICAL BASIS OF THERAPEUTICS" 2001, 10th Edition, McGraw-Hill, New York; and/or are available from the Federal Drug Administration and/or are discussed in the medical literature.

In some aspects, the dose of a telomerase inhibitor, imetelstat sodium, administered to the subject is about 1.0 mg/kg to about 13.0 mg/kg. In other aspects, the dose of a telomerase inhibitor is about 4.5 mg/kg to about 11.7 mg/kg or about 6.0 mg/kg to about 11.7 mg/kg or about 6.5 mg/kg to about 11.7 mg/kg. In some embodiments, the dose of a telomerase inhibitor includes at least about any of 4.7 mg/kg, 4.8 mg/kg, 4.9 mg/kg, 5.0 mg/kg, 5.5 mg/kg, 6.0 mg/kg, 6.1 mg/kg, 6.2 mg/kg, 6.3 mg/kg, 6.4 mg/kg, 6.5 mg/kg, 6.6 mg/kg, 6.7 mg/kg, 6.8 mg/kg, 6.9 mg/kg, 7 mg/kg, 7.1 mg/kg, 7.2 mg/kg, 7.3 mg/kg, 7.4 mg/kg, 7.5 mg/kg, 7.6 mg/kg, 7.7 mg/kg, 7.8 mg/kg, 7.9 mg/kg, 8 mg/kg, 8.1 mg/kg, 8.2 mg/kg, 8.3 mg/kg, 8.4 mg/kg, 8.5 mg/kg, 8.6 mg/kg, 8.7 mg/kg, 8.8 mg/kg, 8.9 mg/kg, 9 mg/kg, 9.1 mg/kg, 9.2 mg/kg, 9.3 mg/kg, 9.4 mg/kg, 9.5 mg/kg, 9.6 mg/kg, 9.7 mg/kg, 9.8 mg/kg, 9.9 mg/kg, 10 mg/kg, 10.1 mg/kg, 10.2 mg/kg, 10.3 mg/kg, 10.4 mg/kg, 10.5 mg/kg, 10.6 mg/kg, 10.7 mg/kg, 10.8 mg/kg, 10.9 mg/kg, 11 mg/kg, 11.1 mg/kg, 11.2 mg/kg, 11.3 mg/kg, 11.4 mg/kg, 11.5 mg/kg, 11.6 mg/kg, 11.7 mg/kg, 11.8 mg/kg, 11.9 mg/kg, 12 mg/kg, 12.1 mg/kg, 12.2 mg/kg, 12.3 mg/kg, 12.4 mg/kg, 12.5 mg/kg, 12.6 mg/kg, 12.7 mg/kg, 12.8 mg/kg, 12.9 mg/kg, or 13 mg/kg.

In some embodiments, the effective amount of a telomerase inhibitor administered to the individual includes at least about any of 1 mg/kg, 2.5 mg/kg, 3.5 mg/kg, 4.7 mg/kg, 5 mg/kg, 6.0 mg/kg, 6.5 mg/kg, 7.5 mg/kg, 9.4 mg/kg, 10 mg/kg, 15 mg/kg, or 20 mg/kg. In some embodiments, the effective amount of a telomerase inhibitor administered to the individual is about any of 1 mg/kg, 2.5 mg/kg, 3.5 mg/kg, 5 mg/kg, 6.5 mg/kg, 7.5 mg/kg, 9.4 mg/kg, 10 mg/kg, 15 mg/kg, or 20 mg/kg. In various embodiments, the effective amount of a telomerase inhibitor administered to the individual includes less than about any of 350 mg/kg, 300 mg/kg, 250 mg/kg, 200 mg/kg, 150 mg/kg, 100 mg/kg, 50 mg/kg, 30 mg/kg, 25 mg/kg, 20 mg/kg, 10 mg/kg, 7.5 mg/kg, 6.5 mg/kg, 5 mg/kg, 3.5 mg/kg, 2.5 mg/kg, 1 mg/kg, or 0.5 mg/kg of a telomerase inhibitor.

Exemplary dosing frequencies for the pharmaceutical composition including a telomerase inhibitor include, but are not limited to, daily; every other day; twice per week; three times per week; weekly without break; weekly, three out of four weeks; once every three weeks; once every two weeks; weekly, two out of three weeks. In some embodiments, the pharmaceutical composition is administered about once every week, once every 2 weeks, once every 3 weeks, once every 4 weeks, once every 5 weeks, once every 6 weeks, once every 7 weeks or once every 8 weeks. In some embodiments, the composition is administered at least about any of 1×, 2×, 3×, 4×, 5×, 6×, or 7× (i.e., daily) a week, or three times daily, two times daily. In some embodiments, the intervals between each administration are less than about any of 6 months, 3 months, 1 month, 20 days, 15 days, 12 days, 10 days, 9 days, 8 days, 7 days, 6 days, 5 days, 4 days, 3 days, 2 days, or 1 day. In some embodiments, the intervals between each administration are more than about any of 1 month, 2 months, 3 months, 4 months, 5 months, 6 months, 8 months, or 12 months. In some embodiments, there is no break in the dosing schedule. In some embodiments, the interval between each administration is no more than about a week.

Telomerase inhibitors such as imetelstat (e.g., imetelstat sodium) can be administered using any appropriate method. For example, telomerase inhibitors such as imetelstat (e.g., imetelstat sodium) can be administered intravenously once every 4 weeks over a period of time (e.g., one, two, three, four, or five hours). In some embodiments, imetelstat is administered intravenously once weekly over a period of about 2 hours at 7-10 mg/kg. In certain embodiments, imetelstat is administered intravenously once every 3 weeks over a period of about 2 hours at 2.5-7 mg/kg. In an embodiment, imetelstat is administered intravenously for a period of about 2 hours once every 4 weeks at 0.5-5 mg/kg. In an embodiment, imetelstat is administered intravenously once every 3 weeks over a period of about 2 hours at about 2.5-10 mg/kg. Alternatively, imetelstat is administered intravenously for a period of about 2 hours once every 4 weeks at about 0.5-9.4 mg/kg.

In certain embodiments of the method, imetelstat is administered for 1, 2, 3, 4, 5, 6, 7, 8 or more than 8 dosage cycles, each cycle comprising: intravenous administration of about 7-10 mg/kg imetelstat once every four weeks, intravenous administration of about 7-10 mg/kg imetelstat once weekly for four weeks, intravenous administration of about 2.5-10 mg/kg imetelstat once every three weeks, or intravenous administration of about 0.5-9.4 mg/kg imetelstat once every four weeks. In certain instance, each dosage cycle comprises intravenous administration of about 7-10 mg/kg imetelstat once every four weeks. In some cases, each dosage cycle comprises intravenous administration of about 7.5 mg/kg imetelstat about once every four weeks.

In one embodiment of the invention, imetelstat is administered intravenously at a dosage of about 7-10 mg/kg imetelstat once every four weeks following premedication with an antihistamine, corticosteroid, or both. In other embodiments, imetelstat is administered intravenously at a dosage of about 7.5 mg/kg, alternatively from about 7.0 mg/kg to about 7.7 mg/kg, imetelstat once every four weeks following premedication with an antihistamine, corticosteroid, or both.

In certain embodiments, imetelstat is administrated at a dosage about 7.5 mg/kg, alternatively from about 7.0 mg/kg to about 7.7 mg/kg, once every four weeks for at least three cycles and then the dosage is increased. In certain embodiments, the dosage of imetelstat may be increased to about 9.4 mg/kg, alternatively from about 8.8 mg/kg to about 9.6 kg/mg, provided ANC and platelet nadir have not dropped between about $1.5 \times 10^9$/L and about $75 \times 10^9$/L, respectively, and there is no grade ≥3 non-hematological toxicity.

It will be appreciated that treatment for cancer sometimes involves multiple "rounds" or "cycles" of administration of a drug, where each cycle comprises administration of the drug one or more times according to a specified schedule (e.g., every three weeks for three consecutive days; once per week; etc.). For example, anti-cancer drugs can be administered for from 1 to 8 cycles, or for a longer period. When more than one drug (e.g., two-drugs) is administered to a subject, each can be administered according to its own schedule (e.g., weekly; once every three weeks; etc.). It will be clear that administration of drugs, even those administered with different periodicity, can be coordinated so that both drugs are administered on the same day at least some of the time or, alternatively, so the drugs are administered on consecutive days at least some of the time.

As is understood in the art, treatment with cancer therapeutic drugs can be suspended temporarily if toxicity is observed, or for the convenience of the patient, without departing from the scope of the invention, and then resumed.

In certain embodiments, the invention relates to a telomerase inhibitor for use in a method of treating myelodysplastic syndrome (MDS), the method comprising administering to a subject in need thereof an effective amount of a telomerase inhibitor; wherein the subject is naive to treatment with an agent selected from a hypomethylating agent (HMA) and lenalidomide. In other embodiments, the invention relates to a telomerase inhibitor for use in a method of treating myelodysplastic syndrome (MDS), the method comprising administering to a subject in need thereof an effective amount of a telomerase inhibitor; wherein the subject is naive to treatment with an agent selected from a HMA, lenalidomide, and combination thereof.

In certain embodiments, the invention relates to a telomerase inhibitor for use in a method as defined in any of the other embodiments.

H. Exemplary Embodiments

Exemplary embodiments of the methods of treating MDS of the invention, which involve administering to a subject in need thereof an effective amount of a telomerase inhibitor whereby the subject is naive to treatment with an agent selected from a hypomethylating agent (HMA) and lenalidomide are shown in Table A below.

Exemplary embodiments include using any of the telomerase inhibitors in Table A to treat any one of the types of MDS shown in Table A in any one of the subjects shown in Table A, whereby the subject is naïve to any one of the treatments shown in Table A. In certain embodiments, one of the administration regimens described in Table A is used. In other embodiments, the methods may be used to treat any one of the types of MDS shown in Table A in any one of subjects shown in Table A using imetelstat (imetelstat sodium), whereby the subject is naïve to any one of the treatments shown in Table A. When imetelstat (imetelstat sodium) is used, any of the administration regimens shown in Table A may be used.

TABLE A

| | Exemplary embodiments of the invention |
|---|---|
| Type of MDS | MDS |
| | Relapsed or refractory MDS |
| | Relapsed MDS |
| | Refractory MDS |
| | MDS relapsed/refractory to erythropoiesis-stimulating agent (ESA) (e.g. erythropoietin-alpha, erythropoietin-beta, darbepoetin, or combination thereof). |
| Subject | low or intermediate-1 IPSS risk MDS subject |
| | low or intermediate-1 IPSS risk MDS subject and transfusion dependent |
| | low or intermediate-1 IPSS risk MDS subject and transfusion dependent with a transfusion requirement of about 4 units or more during the 8 weeks prior to the administration of the telomerase inhibitor |
| | transfusion dependent e.g. transfusion dependent with a transfusion requirement of about 4 units or more during the 8 weeks prior to the administration of the telomerase inhibitor |
| | low or intermediate-1 IPSS risk MDS subject and non-del5q |
| | low or intermediate-1 IPSS risk MDS subject, non-del5q, and transfusion dependent |
| | low or intermediate-1 IPSS risk MDS subject, non-del5q, and transfusion dependent with a transfusion requirement of about 4 units or more during the 8 weeks prior to the administration of the telomerase inhibitor |
| | non-del5q |
| | non-del5q and transfusion dependent |
| | non-del5q and transfusion dependent with a transfusion requirement of about 4 units or more during the 8 weeks prior to the administration of the telomerase inhibitor |
| Subject naive to treatment with | Hypomethylating agent (e.g. decitabine or azacitidine) |
| | Hypomethylating agent (e.g. decitabine or azacitidine) and lenalidomide |
| | decitabine |
| | azacitidine |
| | azacitidine and decitabine |
| | lenalidomide |
| | lenalidomide and decitabine |
| | lenalidomide and azacitidine |
| | lenalidomide, azacitidine, and decitabine |
| Telomerase inhibitor | Any suitable inhibitor or |
| | imetelstat (imetelstat sodium) |
| Administration | Administration of telomerase inhibitor for 1, 2, 3, 4, 5, 6, 7, 8 or more than 8 dosage cycles |
| | Administration of imetelstat (imetelstat sodium) for 1, 2, 3, 4, 5, 6, 7, 8 or more than 8 dosage cycles, each cycle comprising: (a) intravenous administration of about 7-10 mg/kg imetelstat once every four weeks; (b) intravenous administration of about 7-10 mg/kg imetelstat once weekly for four weeks; (c) intravenous administration of about 2.5-10 mg/kg imetelstat once every three weeks; or (d) intravenous administration of about 0.5-9.4 mg/kg imetelstat once every four weeks. |
| | Administration of imetelstat (imetelstat sodium) for 1, 2, 3, 4, 5, 6, 7, 8 or more than 8 dosage cycles, each cycle comprises intravenous administration of about 7-10 mg/kg of imetelstat (imetelstat sodium) once every four weeks |
| | Administration of imetelstat (imetelstat sodium) for 1, 2, 3, 4, 5, 6, 7, 8 or more than 8 dosage cycles, each cycle comprises intravenous administration of about 7.5 mg/kg imetelstat of imetelstat (imetelstat sodium) once every four weeks |
| Pharmacodynamics | Reduction of hTERT RNA expression by 50% or more, such as 60% or more, 70% or more, 80% or more, or 90% or more. |
| | Reduction of hTERT expression by 50% or more, such as 60% or more, 70% or more, 80% or more, or 90% or more. |

The following examples are offered by way of illustration and not by way of limitation.

Examples

Example 1: Efficacy and Safety of Imetelstat in Transfusion-Dependent (TD) Patients with International Prognostic Scoring System (IPSS) Low/Intermediate-1 Risk Myelodysplastic Syndromes that are Relapsed/Refractory to Erythropoiesis-Stimulating Agent (ESA) Treatment (IMerge™)

Introduction

IMerge™: ongoing 2-part, global, study of imetelstat sodium in red blood cell (RBC) transfusion-dependent (TD) patients, ESA-relapsed/refractory, and lower risk MDS. Part 1 consists of an open-label, single-arm design with imetelstat sodium monotherapy. This example provides safety and efficacy findings from 32 patients enrolled in Part 1. A subgroup analysis of patients naive to lenalidomide and hypomethylating agent (HMA) treatment and without del (5q) is also presented. The results suggest improved efficacy among these patients.

Methods

Eligibility:
The eligibility requirements for the study were as follows:
Adults diagnosed with MDS; International Prognostic Scoring System (IPSS) Low or Int-1
Transfusion Dependence (TD), defined as a red blood cell (RBC) transfusion requirement of ≥4 units over 8 weeks prior to study entry.
ESA relapsed or refractory following at least 8 weeks of weekly epoetin alfa 40,000 U or darbepoetin alfa 150 mcg (or equivalent) or serum erythropoietin (sEPO) >500 mU/mL
Any prior therapy (including lenalidomide or HMAs) allowed. Patients with the del(5q) karyotype were allowed to enter irrespective of prior treatment.
Eastern Cooperative Oncology Group (ECOG) score 0-2.
Absolute neutrophil count (ANC) ≥1.5×10$^9$/L and platelets ≥7 5×10$^9$/L independent of growth factor or transfusion support.
Liver function tests: AST, ALT and ALP ≤2.5 times the upper limit of normal (x ULN), total bilirubin ≤3×ULN and direct bilirubin ≤2×ULN (unless due to Gilbert's syndrome).

Treatment:
Imetelstat sodium was administered as a 2-hour IV infusion every 4 weeks at a starting dose of 7.5 mg/kg, following premedication with an antihistamine and corticosteroid. Dose escalation to 9.4 mg/kg was permitted for insufficient response after at least 3 cycles at the initial dose, provided that ANC and platelet nadirs had not dropped below 1.5× 10$^9$/L and 75×10$^9$/L, respectively, and no grade ≥3 non-hematological toxicity. Supportive care, including transfusion and myeloid growth factors as clinically indicated, was permitted.

Endpoints and Analysis:
Primary endpoint: rate of RBC transfusion-independence (TI) lasting ≥8 weeks.
Key secondary endpoints:
Safety;
Rate of ≥24-week TI;
Time to and duration of TI;
Hematologic improvement (HI) rate; and
Rate of complete response (CR) and partial response (PR) per International Working Group (IWG).

Results

Patients
Baseline median RBC transfusion burden, 6 units/8 weeks (range: 4-14)
The baseline characteristics are shown in Table 1 below. The following abbreviations are used in Table 1: Eastern Cooperative Oncology Group Performance Status Score of 0-1 ("ECOG PS 0-1"); refractory anemia with ringed sideroblasts ("RARS"); or refractory cytopenia with multilineage dysplasia and ringed sideroblasts ("RCMD-RS").

TABLE 1

| Baseline characteristics (N = 32) | |
|---|---|
| Median age (range), y | 68.5 (46-83) |
| Male, n (%) | 16 (50) |
| ECOG PS 0-1 (%) | 29 (91) |
| IPSS risk, n (%) | |
| Low | 19 (59) |
| Intermediate-1 | 13 (41) |
| Karyotype | |
| Normal | 17 (53) |
| Any Abnormality | 11 (34) |
| del(5q) | 7 (22) |
| Unknown (missing or no growth) | 4 (13) |
| WHO category, n (%) | |
| RARS/RCMD-RS | 16 (50) |
| All others | 16 (50) |
| sEPO > 500 mU/mL, n (%) | 13* (43) |
| Prior ESA | 28 (88) |
| Prior lenalidomide, n (%) | 12 (38) |
| Prior decitabine or azacitidine | 8 (25) |
| Naive to lenalidomide and HMA and non-del (5q), n (%) | 13 (41) |

*Of 30 patients with sEPO levels reported

Key hematologic criteria: ANC=1,500 and PLT=75,000. Based on the baseline RBC transfusion burden, this was a heavily transfused group of patients.

Results (First Data Snapshot)

Exposure
Median follow-up for this analysis: 66.1 weeks
Median number of treatment cycles: 6.5 (range: 1-20 cycles)
Sixteen patients (50%) had dose reductions and 19 patients (59%) had cycle delays due to adverse events
Seven patients had imetelstat sodium dose escalation to 9.4 mg/kg Efficacy
Table 2 below shows key efficacy outcomes.

TABLE 2

| Key Efficacy Outcomes | | |
|---|---|---|
| Outcomes | All treated (N = 32) | Lenalidomide and HMA naive and non-del(5q) (n = 13) |
| Rate of ≥8-week TI, n (%) | 12* (38) | 7 (54) |
| Mean relative reduction from baseline transfusion burden (%) | −64 | −71 |
| Rate of ≥24-week TI, n (%) | 5 (16) | 4 (31) |
| Median time to onset of TI, weeks | 8.1 | 8.3 |

TABLE 2-continued

Key Efficacy Outcomes

| Outcomes | All treated (N = 32) | Lenalidomide and HMA naive and non-del(5q) (n = 13) |
|---|---|---|
| Median duration of TI, weeks | 23.1 | 42.9 |
| Erythroid HI rate, n (%) | 20† (63) | 9† (69) |
| CR + mCR + PR (per IWG), n (%) | 4 (13) | 3 (23) |

*Results are based on the Oct. 16, 2017 data snapshot ("first data snapshot"), at which one ≥8-week TI had not been fully confirmed based on communication with investigator
†(Includes patients with a transfusion reduction of ≥4 units during the best 8-week on-study interval, as well as those with a hemoglobin increase from pretreatment level.

The primary endpoint of RBC TI lasting ≥8-weeks was achieved in 12/32 (38%) patients.

Figure 1B:
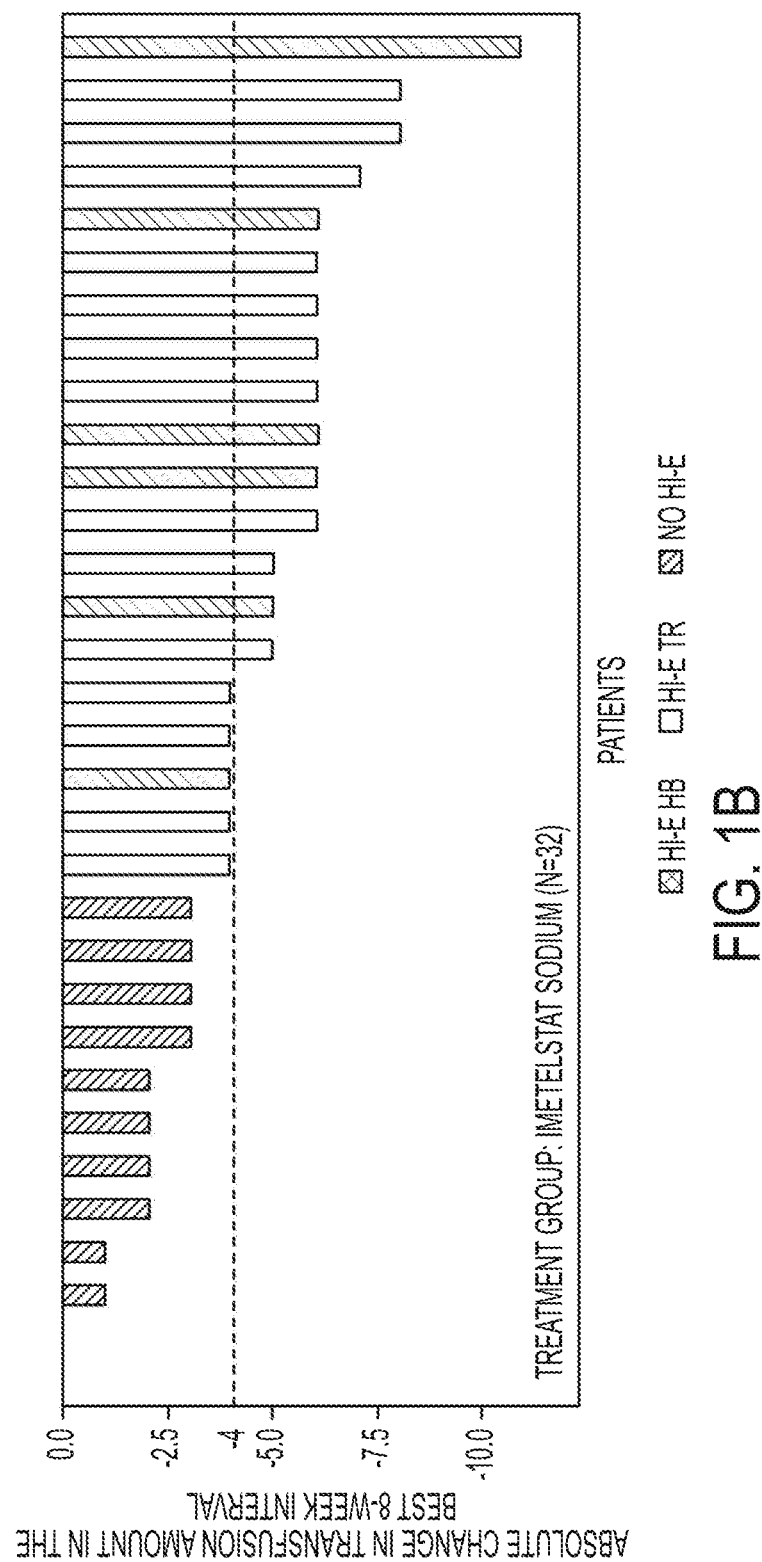
Figure 2:
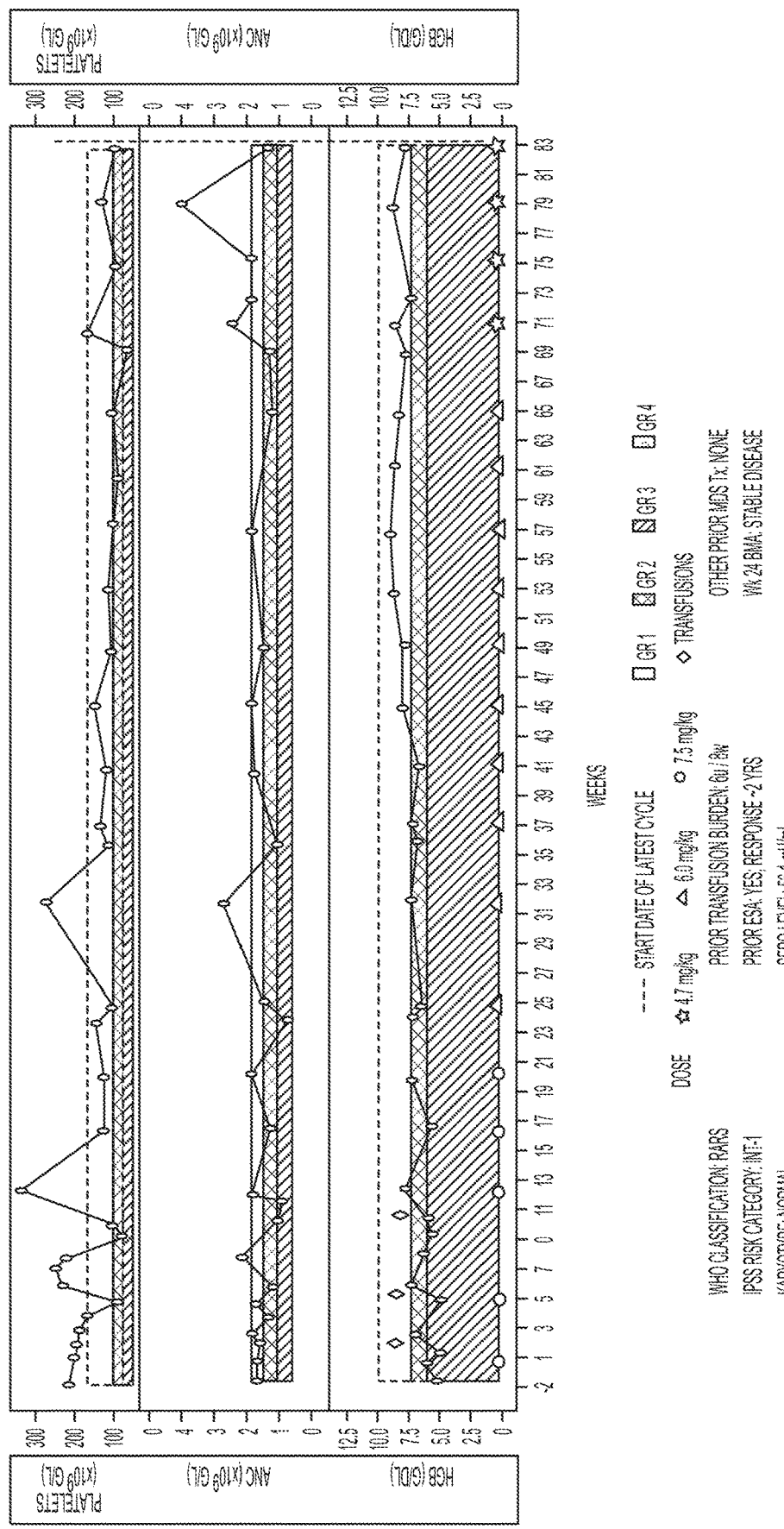
FIG. 2 (first data cut) shows a hematology and imetelstat sodium administration timeline for an exemplary 24-week transfusion independent (TI) responder.

5/32 (16%) achieved 24-week TI (see FIGS. 1A, 1B and FIG. 2). These patients also achieved sustained hemoglobin increases by at least 1.5 g/dL over 8 weeks (HI-E Hb) (HI-E Hb=HI-E with sustained rise in hemoglobin by at least 1.5 g/dL over 8 weeks). The patients' duration of TI (65.1 weeks) exceeded one year.

20/32 patients (63%) had an erythroid hematologic improvement (HI) (see FIG. 1A and FIG. 1B).

In the subset of patients who were naive to lenalidomide and HMAs and who lacked del(5q), 8-week and 24-week TI rates were 54% and 31%, respectively (higher than in the overall population) and the erythroid HI rate was 69% (similar to that reported in the overall population). Complete Response (CR) and marrow CR (mCR) were each reported for 2 patients and there were no Partial Responses (PRs), for a CR+PR+mCR rate of 13%.

One CR and both mCR were in the subset of patients who were naive to lenalidomide and HMAs and who lacked del(5q). 8-week TI did not differ based on the presence of ringed sideroblasts (RS): 38% (6/16) for RS+ and 38% (6/16) for RS−. Response appeared to be independent of sEPO level; of 30 patients with baseline sEPO level reported: 41% (7/17) with sEPO level ≤500 mU/L achieved ≥8-week TI; and 38% (5/13) with sEPO level >500 mU/L achieved ≥8-week TI.

Safety

Cytopenias, particularly neutropenia and thrombocytopenia, were the most frequently reported adverse events overall and in the subset who were naive to lenalidomide and HMAs and lacked del(5q) (see Table 3 below). This subset of patients had a lower incidence of grade ≥3 neutropenia relative to the overall population but similar grade ≥3 thrombocytopenia (see Table 4 below). In most cases, grade ≥3 cytopenias were reversible within 4 weeks without clinical sequelae, and patients were able to continue imetelstat sodium treatment after dose modification.

1 patient (of 22 with neutropenia) experienced neutropenic fever and 2 patients (of 18 with thrombocytopenia) had grade 3 thrombocytopenia concurrent with grade 1 bleeding events that were both considered related to imetelstat sodium; these events recovered without sequelae. 28 patients (88%) had liver function test (LFT) elevations by at least one grade. These events were generally grade 1 or 2 and reversible. Four patients (including 3 in the subset of patients who were naive to lenalidomide and HMAs and who lacked del[5q]) had grade 3 worsening of aspartate aminotransferase (AST) and/or alanine aminotransferase (ALT), and 1 of these patients had grade 3 worsening of bilirubin; all of which were reversible.

Table 3 shows the most common treatment emergent adverse events. Table 4 shows the maximum grade change in cytopenias from baseline.

TABLE 3

Most Common Treatment-Emergent Adverse Events (≥10% of Patients in All Treated Patients)

| | All Treated (N = 32) | Lenalidomide and HMA naive and non-del(5q) (n = 13) |
|---|---|---|
| Patients with ≥1 treatment emergent adverse events ("AEs"), n (%) | 31 (97) | 12 (92) |
| Neutropenia | 22 (69) | 7 (54) |
| Thrombocytopenia | 18 (56) | 8 (62) |
| Headache | 8 (25) | 2 (15) |
| Alanine aminotransferase ("ALT") increased | 6 (19) | 3 (23) |
| Aspartate aminotransferase ("AST") increased | 5 (16) | 3 (23) |
| Leukopenia | 5 (16) | 2 (15) |
| Muscle spasms | 5 (16) | 2 (15) |
| Anemia | 4 (13) | 2 (15) |
| Asthenia | 4 (13) | 4 (31) |
| Constipation | 4 (13) | 2 (15) |
| Cough | 4 (13) | 1 (8) |
| Diarrhea | 4 (13) | 1 (8) |
| Dyspnea | 4 (13) | 2 (15) |
| Influenza like illness | 4 (13) | 1 (8) |
| Nausea | 4 (13) | 2 (15) |
| Peripheral edema | 4 (13) | 2 (15) |
| Viral URI | 4 (13) | 4 (31) |

TABLE 4

Maximum Grade Change in Cytopenias From Baseline

| | All Treated (N = 32) | Lenalidomide and HMA naive and non-del(5q) (n = 13) |
|---|---|---|
| Neutrophils, n (%) | | |
| No worsening | 4 (13) | 3 (23) |
| 1 | 3 (9) | 1 (8) |
| 2 | 4 (13) | 2 (15) |
| 3 | 8 (25) | 2 (15) |
| 4 | 13 (41) | 5 (38) |
| Platelets, n (%) | | |
| No worsening | 7 (22) | 3 (23) |
| 1 | 2 (6) | 1 (8) |
| 2 | 7 (22) | 2 (5) |
| 3 | 10 (31) | 5 (38) |
| 4 | 6 (19) | 2 (15) |

Results in Table 4 are based on the first data snapshot.

Results (Second Data Snapshot)

Exposure

Median follow-up for this analysis: 95 weeks

Median number of treatment cycles: 6.5 (range: 1-28 cycles)

Sixteen patients (50%) had dose reductions and 19 patients (59%) had cycle delays Seven patients had imetelstat sodium dose escalation to 9.4 mg/kg Efficiency Table 5 below shows key efficiency outcomes at the second data snapshot.

TABLE 5

Key Efficacy Outcomes

| Parameters | All Treated (N = 32) | Lenalidomide and HMA naive and non-del(5q) (n = 13) |
|---|---|---|
| Rate of 8-week TI, n (%) | 11 (34) | 7 (54) |
| Rate of 24-week TI, n (%) | 5 (16) | 4 (31) |
| Median time to onset of TI (range), weeks | 8.0 (0.1-33.1) | 8.3 (0.1-33.1) |
| Median duration of TI (range), weeks | 23.1 (8-105) | 42.9 (8-105) |
| Rate of transfusion reduction (HI-E), n (%) | 19 (59) | 9 (69) |
| Mean relative reduction of RBC transfusion burden from baseline, % | −60 | −71 |
| CR + marrow CR + PR (per IWG), n (%) | 6 (19) | 4 (31) |

*Results are based on the May 10, 2018 data snapshot ("second data snapshot")
†(Includes patients with a transfusion reduction of ≥4 units during the best 8-week on-study interval, as well as those with a hemoglobin increase from pretreatment level.

Maximum duration of follow-up from responding patient was 115 weeks or 26 months.

Among the seven subjects who had dose escalation, one subject reached 8-week TI and three subjects reached HI-E. The median number of treatment cycles for subgroup was 8 cycles. Median duration of therapy overall and subgroup was 24 weeks and 29 weeks, respectively.

Figure 3A:
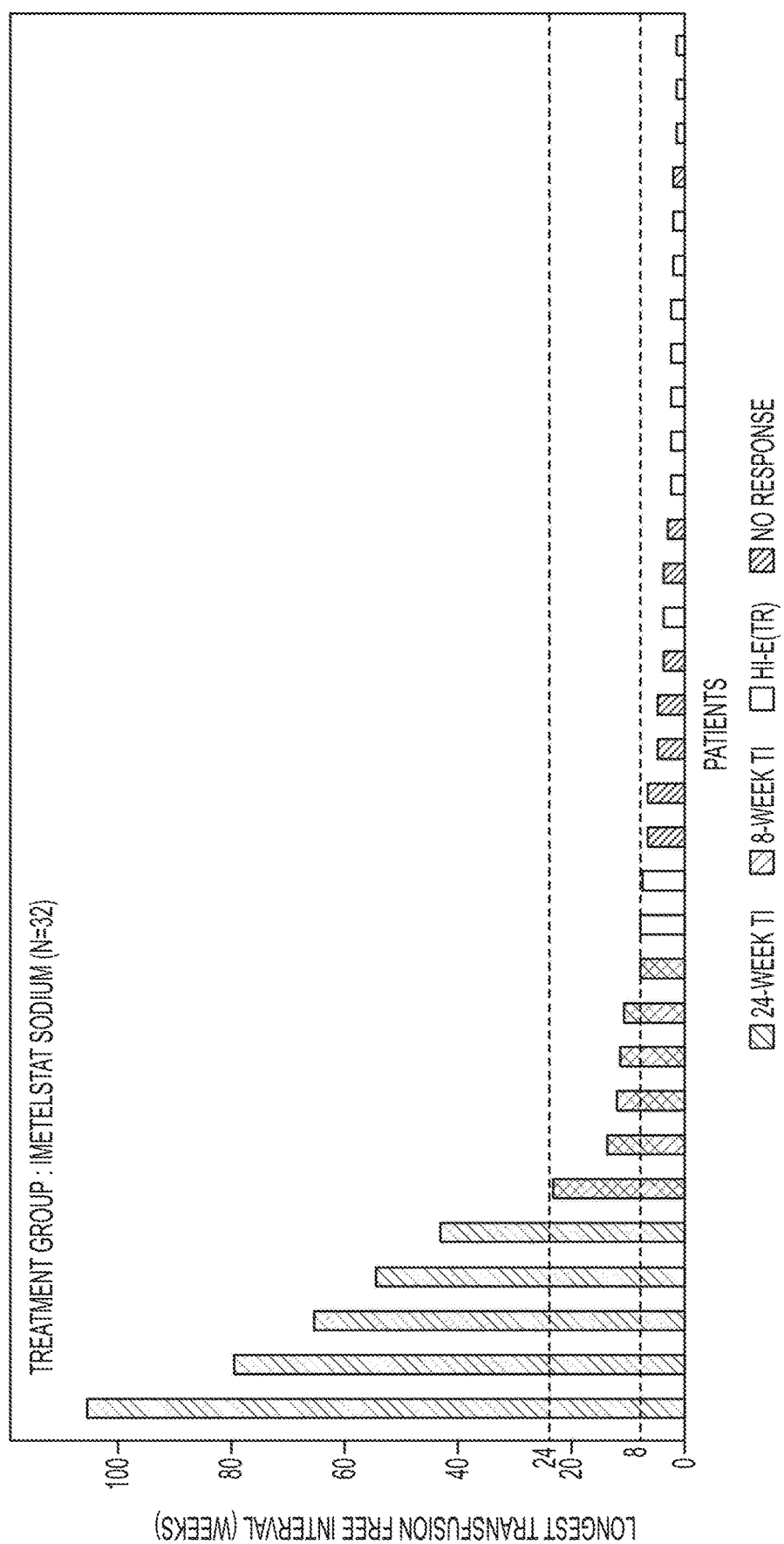
FIGS. 3A and 3B (second data cut) show waterfall plots of the longest transfusion-free interval (FIG. 3A) and absolute change in transfusion amount in the best 8-week interval (FIG. 3B) in a study of imetelstat sodium in red blood cell (RBC) transfusion-dependent (TD) patients as described herein in the experimental section. HI-E=hematologic improvement-erythroid based on a Hb rise of at least 1.5 g/dL above the pretreatment level for at least 8 weeks or reduction of at least 4 units of RBC transfusions/8 weeks compared with the prior RBC transfusion burden (criterion adapted from IWG 2006); TI=transfusion independence; TR=transfusion reduction by at least 4 units over 8 weeks.

FIG. 3A shows the longest transfusion free interval at the second data snapshot. Three of the five patients at 24-week TI are still on treatment. The data shown in FIG. 3A are summarized in Table 6 below:

TABLE 6

Longest Transfusion-Free Interval

| Parameters | All Treated (N = 32) |
|---|---|
| Rate of 8-week TI, n (%) | 11 (34) |
| Rate of 24-week TI, n (%) | 5 (16) |
| Median time to onset of TI (range), weeks | 8.0 (0.1-33.1) |
| Median duration of TI (range), weeks | 23.1 (8-105) |

Figure 3B:
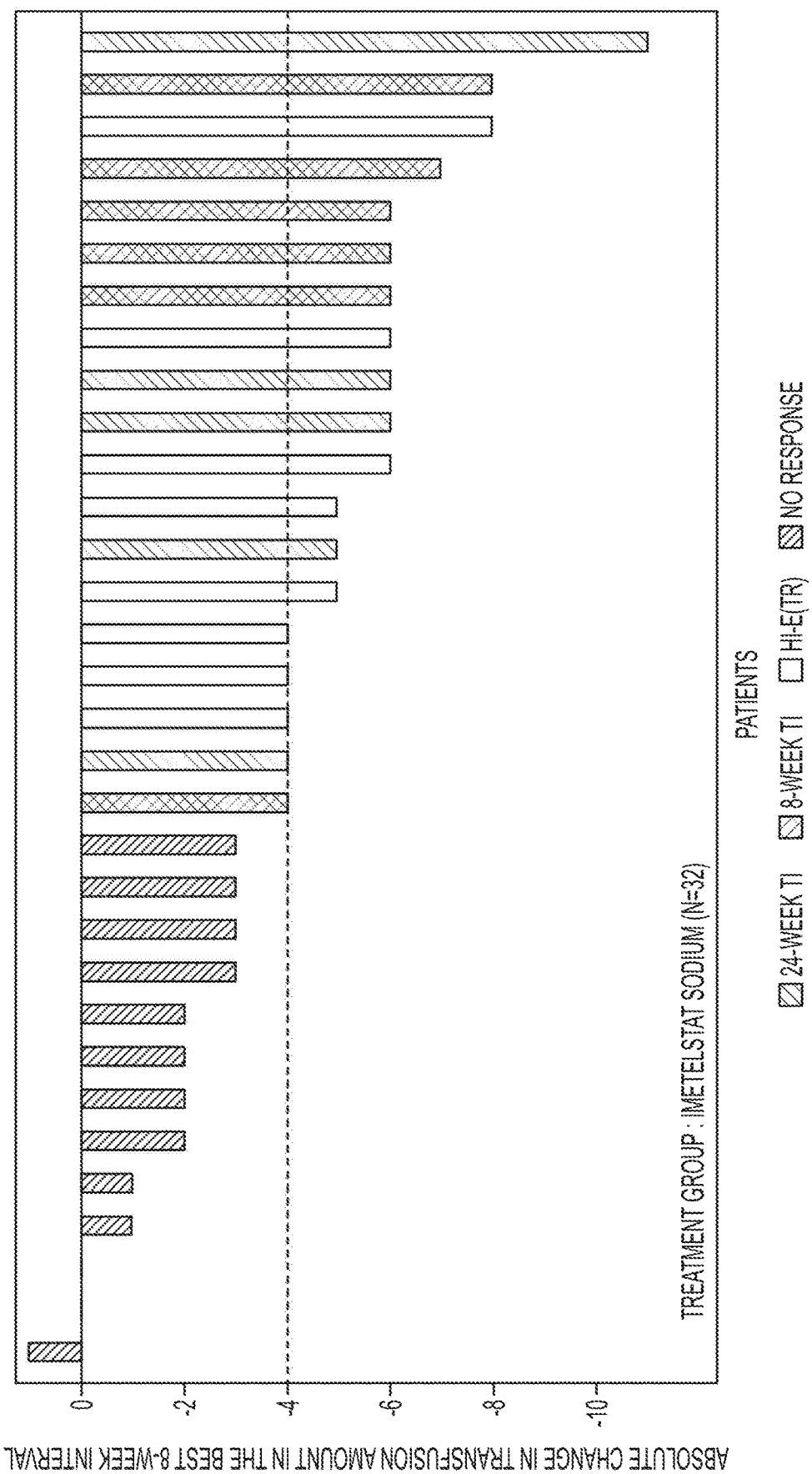

FIG. 3B shows the absolute change in transfusion amount in the best 8-week interval. One patient with transfusion burden of 10 went down to 0. Patients not achieving TI (HI-E (TR)) had some fairly meaningful reductions in transfusion burden. The data shown in FIG. 3B are summarized in Table 7 below:

TABLE 7

Absolute Change in Transfusion Amount in the Best 8-Week Interval

| Parameters | All Treated (N = 32) |
|---|---|
| Rate of transfusion reduction (HI-E), n (%) | 19 (59) |
| Mean relative reduction of RBC transfusion burden from baseline, % | −60 |

Figure 4:
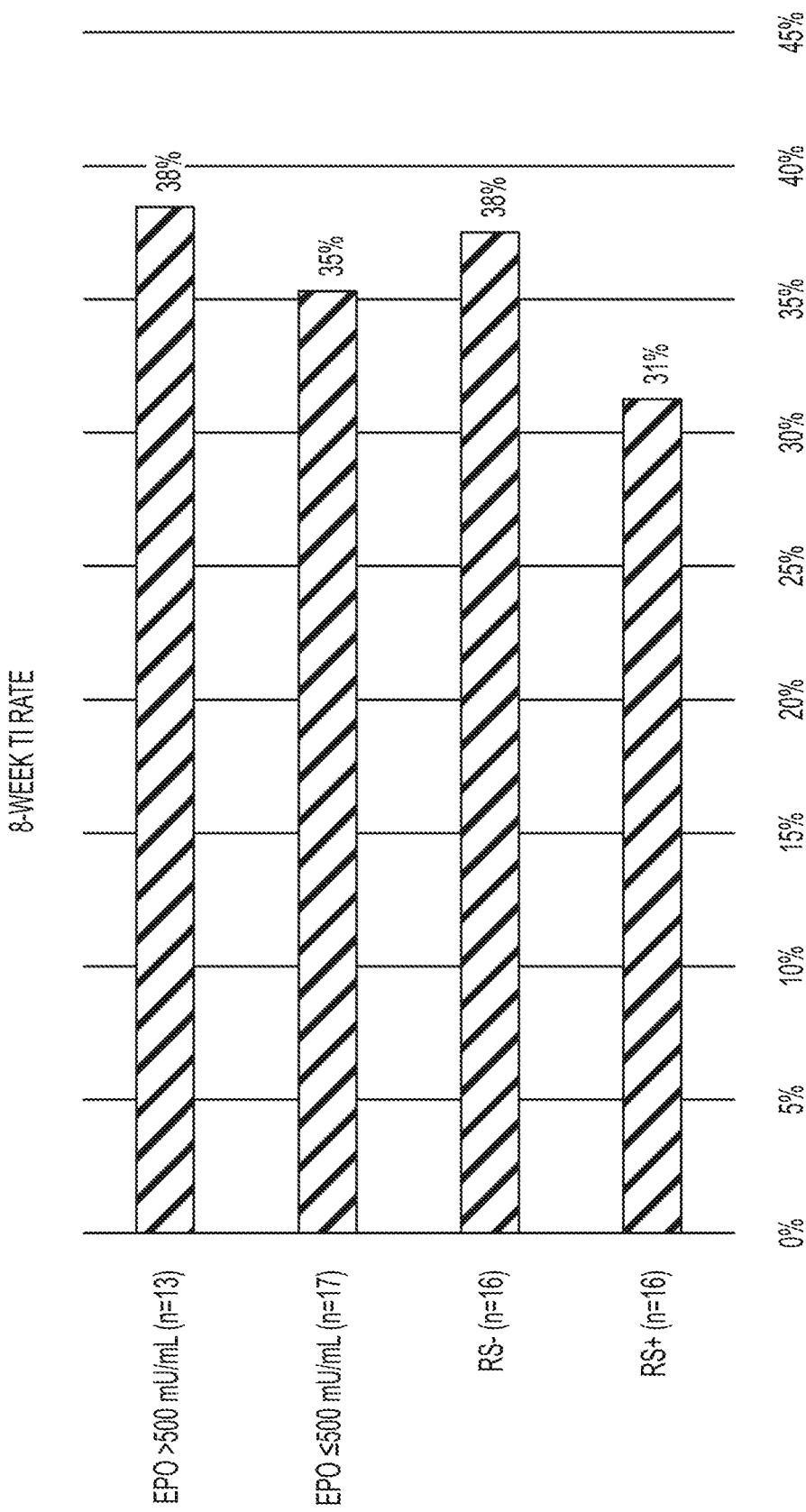
FIG. 4 (second data cut) shows the Efficacy Results in EPO and RS Subgroups.
Figure 5:
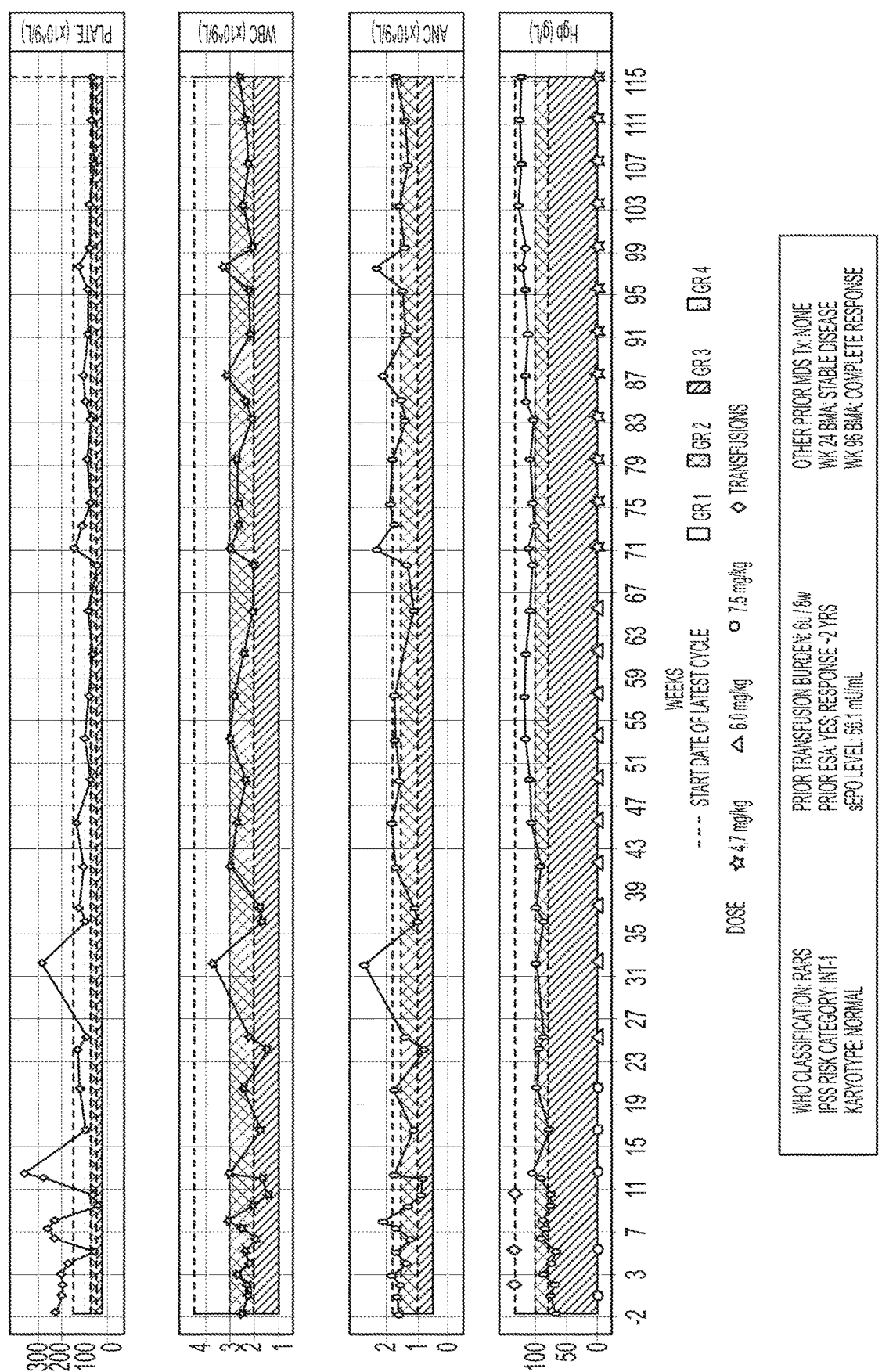
FIG. 5 (second data cut) shows a hematology and imetelstat sodium administration timeline for up to 115 weeks for an exemplary 24-week transfusion independent (TI) responder.
Figure 6:
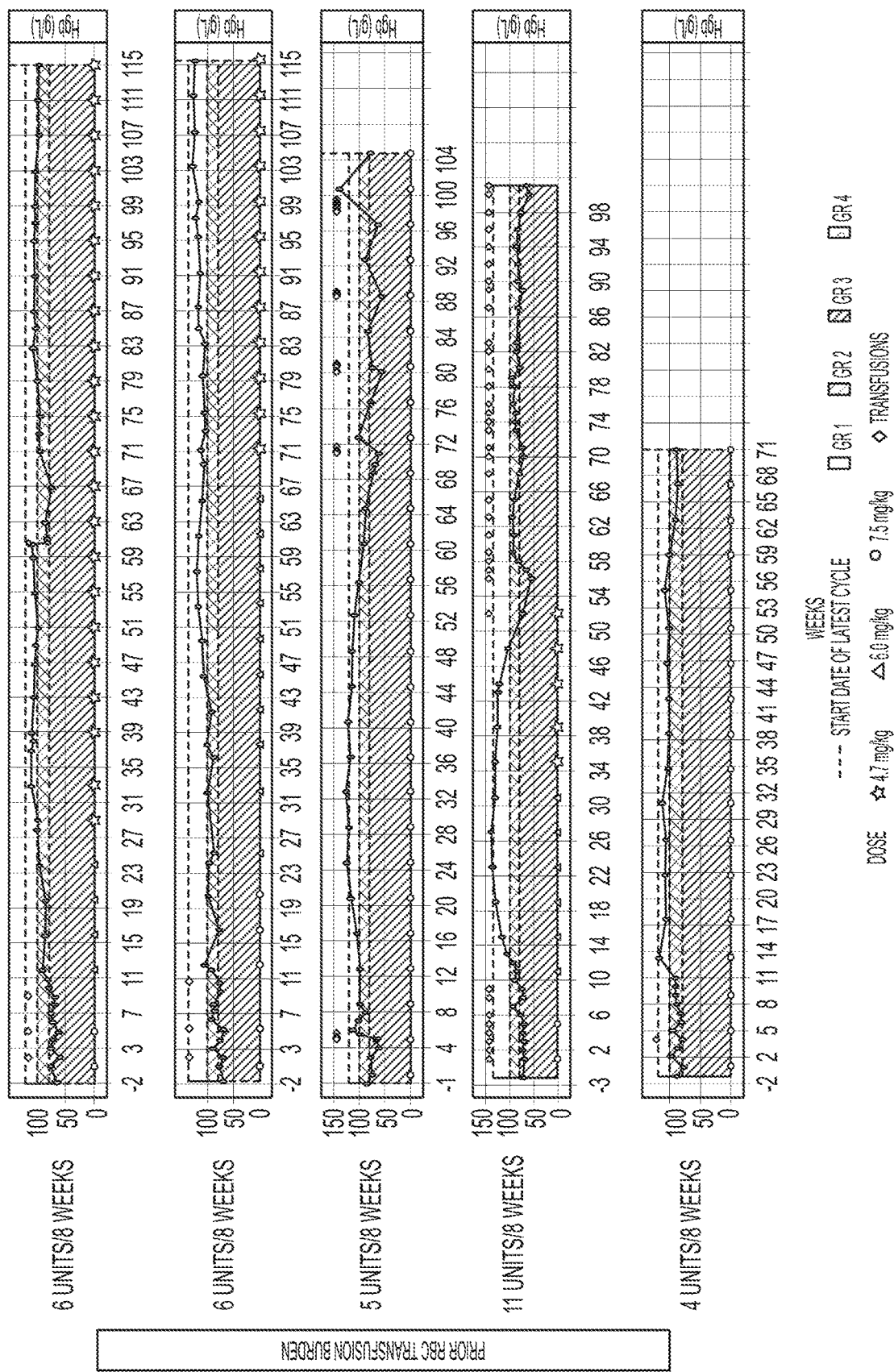
FIG. 6 (second data cut) shows the hemoglobin and imetelstat sodium dosing among patients with durable TI.

FIG. 4 shows the efficacy results in EPO and RS Subgroups at the second data snapshot. Similar efficacy was observed across these subgroups. FIG. 5 shows hematology and imetelstat sodium administration by patients over time at the second data snapshot. FIG. 6 shows the hemoglobin and imetelstat sodium dosing among patients with durable TI. The top three patients in FIG. 6 are still receiving treatment. The top two subjects in FIG. 6 have the longest follow-up.

Safety

Safety findings for those who were lenalidomide/HMA-naive/non-del(5q) were similar to the overall study population.

Table 8 shows the most common treatment emergent adverse events at the second data snapshot. Table 9 shows the occurrence and reversibility of Grade 3/4 Cytopenias. Table 10 shows the maximum post-baseline Common Terminology Criteria for Adverse Events (CTCAE) grade, worsened since baselines for cytopenia by population and safety analysis set at the second data snapshot.

TABLE 8

Most Common Treatment-Emergent Adverse Events (≥10% of Patients in All Treated Patients)

| | All Treated (N = 32) | Lenalidomide and HMA naive and non-del(5q) (n = 13) |
|---|---|---|
| Patients with ≥1 treatment emergent adverse events ("AEs"), n (%) | 31 (97) | 12 (92) |
| Neutropenia | 23 (72) | 7 (54) |
| Thrombocytopenia | 18 (56) | 8 (62) |
| Headache | 8 (25) | 2 (15) |
| Alanine aminotransferase ("ALT") increased | 6 (19) | 3 (23) |
| Aspartate aminotransferase ("AST") increased | 5 (16) | 3 (23) |
| Leukopenia | 5 (16) | 2 (15) |
| Muscle spasms | 5 (16) | 2 (15) |
| Diarrhea | 5 (16) | 2 (15) |
| Anemia | 4 (13) | 2 (15) |
| Asthenia | 4 (13) | 4 (31) |
| Back pain | 4 (13) | 2 (15) |
| Constipation | 4 (13) | 2 (15) |
| Cough | 4 (13) | 1 (8) |
| Dyspnea | 4 (13) | 2 (15) |
| Influenza like illness | 4 (13) | 1 (8) |
| Nausea | 4 (13) | 2 (15) |
| Peripheral edema | 4 (13) | 2 (15) |
| Viral URI | 4 (13) | 4 (31) |

TABLE 9

Occurrence and Reversibility of Grade 3/4 Cytopenias

| | All Treated (N = 32) | Lenalidomide and HMA naive and Non-del(5q) (n = 13) |
|---|---|---|
| Neutrophils, n (%) | | |
| Grade 3 | 8 (25) | 2 (15) |
| Recovered <4 weeks | 4 (50) | 1 (50) |
| Grade 4 | 13 (41) | 5 (38) |
| Recovered <4 weeks | 12 (92) | 5 (100) |
| Platelets, n (%) | | |
| Grade 3 | 10 (31) | 5 (38) |
| Recovered <4 weeks | 9 (90) | 5 (100) |
| Grade 4 | 8 (25) | 3 (23) |
| Recovered <4 weeks | 6 (75) | 3 (100) |

Eleven patients received G-CSF during the study for treatment of an adverse event or ongoing medical history (n=10) or as prophylaxis (n=1).

TABLE 10

Maximum Post-baseline CTCAE Grade, Worsened Since Baseline for Cytopenia by Population; Safety Analysis Set

|  | All Subjects | Target Population | Other Subjects |
|---|---|---|---|
| Analysis set: safety | 32 | 13 | 19 |
| Neutrophils (×10E9/L) | | | |
| No worsening | 4 (12.5%) | 3 (23.1%) | 1 (5.3%) |
| 1 | 3 (9.4%) | 1 (7.7%) | 2 (10.5%) |
| 2 | 4 (12.5%) | 2 (15.4%) | 2 (10.5%) |
| 3 | 8 (25.0%) | 2 (15.4%) | 6 (31.6%) |
| 4 | 13 (40.6%) | 5 (38.5%) | 8 (42.1%) |
| Platelets (×10E9/L) | | | |
| No worsening | 5 (15.6%) | 2 (15.4%) | 3 (15.8%) |
| 1 | 2 (6.3%) | 1 (7.7%) | 1 (5.3%) |
| 2 | 7 (21.9%) | 2 (15.4%) | 5 (26.3%) |
| 3 | 10 (31.3%) | 5 (38.5%) | 5 (26.3%) |
| 4 | 8 (25.0%) | 3 (23.1%) | 5 (26.3%) |

Note:
Worsened defined as CTCAE grade elevated after baseline. The grade 1-4 summaries categorize subjects according to the maximum grade lab among those labs that have worsened since baseline.
Note the target population includes the subjects who had neither prior HMA nor Len use and no del(5q) at baseline.
Data as per snapshot on May 10, 2018 ("second data snapshot")

Observations (Based on Both Data Snapshots)

The safety and efficacy data for the 32 patients in Part 1 of the study support continued investigation of imetelstat sodium using the current dosing regimen of 7.5 mg/kg every 4 weeks.

At the first data snapshot, 8-week RBC TI was demonstrated in 38% and erythroid HI in 63% of IPSS Low/Int-1 RBC transfusion dependent MDS patients relapsed/refractory to ESA. Durable 24-week TI, with sustained rises in Hb, was observed in 16% of patients.

At the first data snapshot, 54% RBC TI was observed in the 13 patients without del(5q) and without prior exposure to either lenalidomide or HMA (compared to 38% in overall population), and responses were more durable (24-week TI rate of 31%).

Overall, 8-week TI observed in 34% of all patients, with a 24-week TI rate of 16%. The median time to TI was 8.0 weeks. The median duration of TI was 23.1 weeks.

For those patients who were lenalidomide/HMA-naive and non-del(5q), the 8-week and 24-week TI rates were 54% and 31%, respectively. For these patients, the median duration of TI was 42.9 weeks.

Overall, TR (HI-E) was observed in 59% of all patients. The mean relative reduction of RBC transfusion burden from baseline was 60%.

These results support further study of imetelstat sodium (7.5 mg/kg/4 weeks) in IPSS Low/Int-1, TD, ESA-relapsed/refractory MDS. In RBC TD patients with LR-MDS (median: 6 U/8 weeks), imetelstat sodium treatment resulted in erythroid improvement in a majority of patients.

This study was repeated for the target population of 13 subjects with non-del(5q) MDS and without prior exposure to either an HMA or lenalidomide. In this target population, 53.8% achieved the primary endpoint of 8-week RBC TI, compared with 21.1% of other subjects not in the target population. The responses were more durable in the target population than in other subjects (median duration, 42.9 vs 13.9 weeks) and more subjects in the target population achieved 24-week RBC TI (30.8% vs 5.3%). The target population exhibited a comparable or better safety profile for cytopenias and other adverse events, and cytopenias appeared to resolve faster in the target population.

Example 2: Results at Third Data Snapshot

A third data snapshot was performed, with a clinical cutoff of Oct. 26, 2018. An additional 25 lenalidomide and HMA naïve patients without del(5q) were enrolled and updated results were compiled for this group in combination with the initial 13 lenalidomide and HMA naïve patients without del(5q) described above. N=38 patients in total.

Median follow-up for the initial 13 patients was 29.1 months. Median follow-up for the additional 25 patients was 8.7 months.

Median number of treatment cycles: 8.0 (range: 1-34) cycles. Mean dose intensity was 6.9 mg/kg/cycle.

TABLE 11

IMerge: Key Efficacy Outcomes

| Parameters | N = 38 |
|---|---|
| Rate of 8-week TI, n (%) | 14 (37) |
| Rate of 24-week TI, n (%) | 10 (26) |
| Median time to onset of TI (range), weeks | 8.1 (0.1-33.1) |
| Median duration of TI (range), weeks | NE (17.0-NE) |
| Rate of transfusion reduction (HI-E), n (%) | 27 (71) |
| Mean relative reduction of RBC transfusion burden from baseline, % | −68 |
| CR + marrow CR + PR (per IWG), n (%) | 8 (21) |

CR, complete remission; HI-E, hematologic improvement-erythroid; IWG, International Working Group; NE, not estimable; PR, partial remission; RBC, red blood cell; TI, transfusion independence.

Example 3: Results at Fourth Data Snapshot

A fourth data snapshot was performed, with a clinical cutoff of Jan. 23, 2019 to report updated efficacy data with a median follow-up of 12.1 months in 38 LR non-del(5q) MDS patients, relapsed/refractory to ESA and naïve to lenalidomide/HMA from the open-label, single-arm Part 1 of the IMerge™ study.

Methods

Part 1 of the IMerge™ study included patients with low or intermediate-1 IPSS risk MDS (LR-MDS), who were heavily transfused (≥4 U/8 weeks), were relapsed/refractory to ESA or had sEPO >500 mU/mL. Imetelstat 7.5 mg/kg was administered IV every 4 weeks. The primary endpoint was 8-week Transfusion Independence (TI) rate; key secondary endpoints included 24-week TI rate, safety, duration of TI, and hematologic improvement (HI) rate. Among the initially enrolled patients, higher 8-week TI rate was observed in the non-del5q, lenalidomide/HMA naive patients. Therefore, the study was amended to subsequently enroll only these patients. From a total of 57 patients enrolled in Part 1, 38 were non-del(5q), lenalidomide/HMA naïve patients (13 in the initial and 25 in the expansion cohort). Long-term efficacy, safety and biomarker data from these 38 patients is reported.

Results

Median prior RBC transfusion burden was 8 Units/8 weeks (range 4-14), 37% of the patients had IPSS Int-1; 71% had WHO 2008 RARS (refractory anemia with ringed sideroblasts) or RCMD-RS (refractory cytopenia with multilineage dysplasia and ringed sideroblasts) subtype and 32% with evaluable sEPO (serum erythropoietin) levels had baseline level >500 mU/mL.

As of Jan. 23, 2019, median follow-up was 12.1 months; 30.4 for the initial 13 patients and 11.6 months for the additional 25 patients, respectively. The 8-week TI rate was 45% (17/38) and median TI duration was 8.5 months (range 1.8-32.4). Of the 17 responding patients, 10 (59%) were transfusion free for over 6-months. The 8-week TI rate did not differ based on the presence of ring sideroblasts or baseline sEPO levels. The 24-week TI rate was 26% (10/38), with median duration of 10.5 months (range 8.3-32.4). 68% (26/38) achieved erythroid hematologic improvement (HI) defined as ≥50% reduction in transfusion burden for at least 8 weeks. The most frequently reported adverse events were manageable and reversible grade ≥3 cytopenias.

SUMMARY

In high RBC transfusion burden patients with non-del(5q) LR-MDS relapsed/refractory to ESA and naive to lenalidomide/HMA, single-agent imetelstat yielded 8-week TI rate of 45%, with a median duration of 8.5 months (range 1.8-32.4). The 24-week TI rate was 26% with median duration of 10.5 months (range 8.3-32.4 months). All patients with IPSS-R intermediate and poor cytogenetic risk responded. Biomarker analyses of telomerase activity and mutation allele burden indicate an effect on the malignant mutant clone, as described below.

Example 4: Biomarker Data

Various biomarkers were monitored and evaluated during the course of the IMerge™ study, including telomerase hTERT RNA levels, telomerase activity (TA), cytogenetic data and mutation data. hTERT RNA expression levels were measured from whole blood samples collected from patients pre- and post-treatment. The results are summarized below.

Greenberg et al. ("Revised International Prognostic Scoring System for Myelodysplastic Syndromes", Blood. 2012 Sep. 20; 120(12): 2454-2465), the disclosure of which is herein incorporated by reference in its entirety, describes the Revised International Prognostic Scoring System (IPSS-R) for assessing prognosis of primary untreated adult patients with MDS. Table 2 of Greenberg et al. sets forth an MDS Cytogenetic Scoring System, which is reproduced below as Table 12 and was utilized to classify patients of the IMerge™ study.

TABLE 12

MDS Cytogenetic Scoring System of Greenberg et al.

| Prognostic subgroups, % of patients | Cytogenetic abnormalities | Median survival,* years | Median AML evolution, 25%,* years | Hazard ratios OS/AML* | Hazard ratios OS/AML† |
|---|---|---|---|---|---|
| Very good (4%*/3%†) | −Y, del(11q) | 5.4 | NR | 0.7/0.4 | 0.5/0.5 |
| Good (72%*/66%†) | Normal, del(5q), del(12p), del(20q), double including del(5q) | 4.8 | 9.4 | 1/1 | 1/1 |
| Intermediate (13%*/19%†) | del(7q), +8, +19, i(17q), any other single or double independent clones | 2.7 | 2.5 | 1.5/1.8 | 1.6/2.2 |
| Poor (4%*/5%†) | −7, inv(3)/t(3q)/del(3q), double including −7/del(7q), complex: 3 abnormalities | 1.5 | 1.7 | 2.3/2.3 | 2.6/3.4 |
| Very poor (7%*/7%†) | Complex: >3 abnormalities | 0.7 | 0.7 | 3.8/3.6 | 4.2/4.9 |

OS indicates overall survival; and NR, not reached.
*Data from patients in this International Working Group for Prognosis in MDS (IWG-PM) database, multivariate analysis (n = 7012).
†Data (n = 2754) from Schanz et al. ("New comprehensive cytogenetic scoring system for primary myelodysplastic syndromes and oligoblastic AML following MDS derived from an international database merge." J. Clin. Oncol. 2012; 30(8): 820-829).

PD Effect: Decrease in Telomerase hTERT RNA Level

TABLE 13 hTERT RNA Expression Analysis (hTERT) at third data snapshot
Subjects with hTERT RNA expression decreases from baseline

| | N with data | hTERT >= 50% decrease | Any Decrease in hTERT |
|---|---|---|---|
| Baseline | 35 | | |
| Cycle 1 Day 1-24 hr | 30 | 9 (30.0%) | 18 (60.0%) |
| Cycle 1 Day 8 | 29 | 10 (34.5%) | 15 (51.7%) |
| Cycle 2 Day 8 | 30 | 10 (33.3%) | 18 (60.0%) |
| Any timepoint during cycle 1-2 (C1-C2) | 34 | 18 (52.9%) | 25 (73.5%) |

Figure 7:
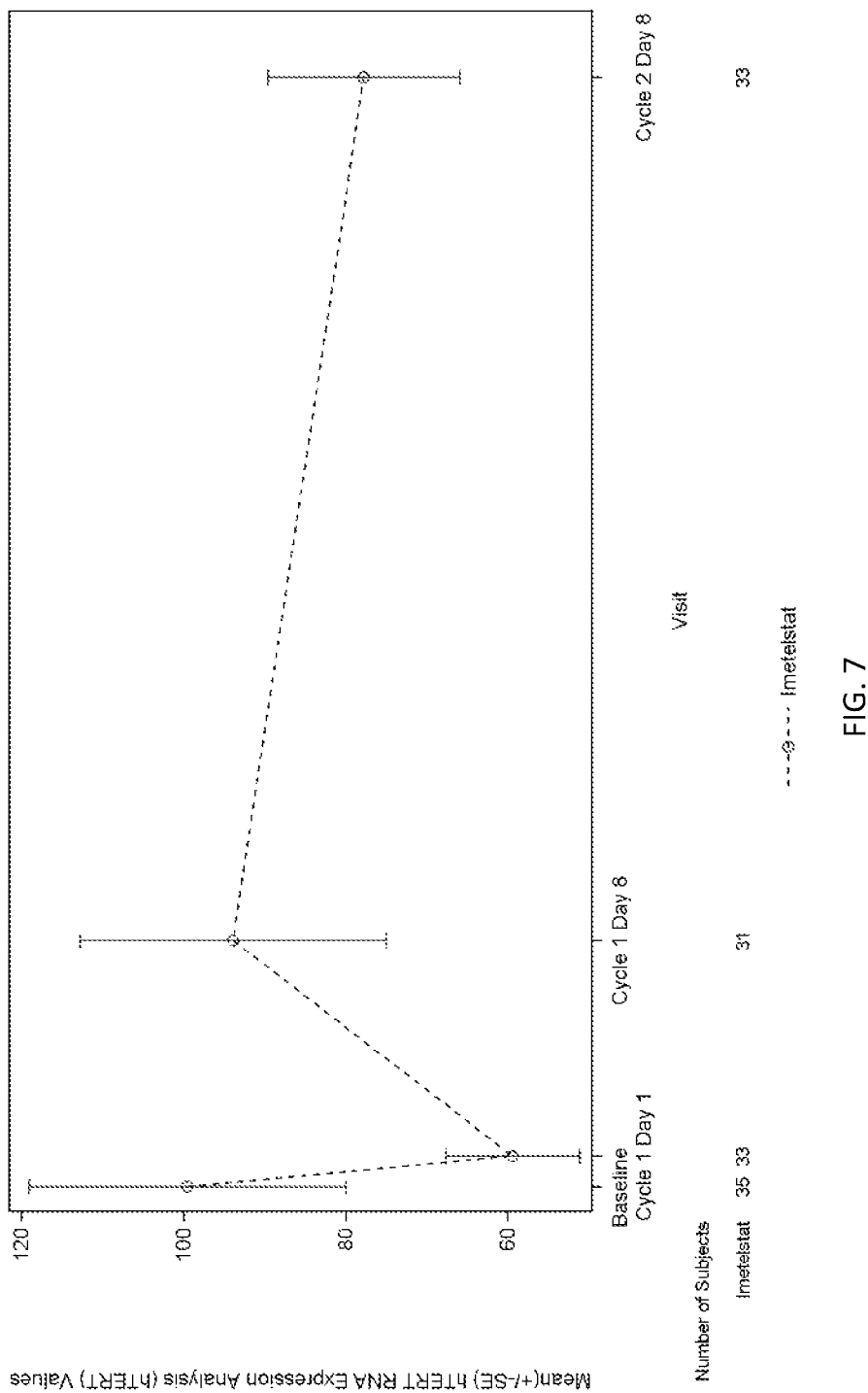
FIG. 7 (fourth data cut) shows that mean hTERT RNA expression levels decrease from baseline prior to treatment among patients during cycle 1 and 2 of the study.

At the fourth data snapshot, post treatment decrease in telomerase hTERT RNA level was observed in 25/34 (73.5%) patients with available sample. See also FIG. 7.

Association Between hTERT Reduction and Response

A higher % of subjects achieved >=50% decrease in hTERT RNA expression levels in 8-week transfusion independence (TI) responders than in non-responders.

TABLE 14 hTERT Reduction at least 50% from baseline
by TI response at third data snapshot.

| 8-wk TI Response | Part 1 target population | Part 1 expansion | Total |
|---|---|---|---|
| Yes | 3/7 (42.9%) | 6/7 (85.7%) | 9/14 (64.3%) |
| No | 1/6 (16.7%) | 8/18 (44.4%) | 9/24 (37.5%) |

PD Effect: Telomerase Activity (TA)

TA decreased post-treatment in some patients.

TABLE 15

Subjects with telomerase activity (TA) decreases from baseline at third data snapshot.

|  | N with data | TA >= 50% decrease | TA >= 30% decrease |
|---|---|---|---|
| Baseline | 16 |  |  |
| Cycle 1 Day 1-24 hr | 5 | 1 (20%) | 3 (60%) |
| Cycle 1 Day 8 | 6 | 2 (33%) | 3 (50%) |

Change in Mutation Variant Frequency

At third data snapshot, 6 subjects had SF3B1 mutations at baseline, reduction of variant frequency was observed in 2 subjects, which had the longest TI duration. One of the subjects had reduction in DNMT3A mutation, and substantial reduction in bone marrow ringed sideroblasts (75% to 3%).

At fourth data snapshot, among seven patients with pre- and post-treatment mutation analyses, six had SF3B1 mutations at baseline, and decrease in the mutation variant allele frequency was observed in 2 patients that had longest TI duration on study.

Cytogenetic Risk

Patients were classified according to the revised International Prognostic Scoring System (IPSS-R) as shown in Table 12.

At the fourth data snapshot, 6 out of 38 patients had IPSS-R intermediate/poor cytogenetic risk and 5 out of 6 patents achieved 8-week TI; 2/6 patients achieved partial cytogenetic response.

SUMMARY

Decrease in telomerase activity/hTERT RNA level post treatment was observed in a subset of subjects indicating PD effect of imetetstat. Subjects that achieved >50% reduction in hTERT were enriched in 8-wk TI responders compared to non-responders Majority of subjects are in good or intermediate cytogenetic risk categories, have observed 8-wk Transfusion Independence (TI) response. At the third data snapshot, two subjects with poor cytogenetic risk did not have a TI response. However, by the fourth data snapshot, of the 6 out of 38 patients who had IPSS-R intermediate/poor cytogenetic risk, 5 out of 6 patents achieved 8-week TI; 2/6 patients achieved partial cytogenetic response.

Among 7 subjects with pre- and post-treatment mutation samples, six had SF3B1 mutations at baseline, and change in the mutation variant frequency observed in patients with the longest TI duration.

Example 5: Treatment with Imetelstat of Heavily Transfused Non-Del(5q) Lower Risk Myelodysplastic Syndromes Patients that are Relapsed/Refractory to Erythropoiesis-Stimulating Agents (ESA)

This example provides safety and efficacy findings from 38 patients enrolled in IMerge™, the study directive being described in greater detail above. The results provided by this example demonstrate that treatment with imetelstat results in meaningful and durable transfusion independence is this patient group.

Methods

Eligibility:

The eligibility requirements for the study were as follows:
Adults diagnosed with MDS; International Prognostic Scoring System (IPSS) Low or Int-1
Transfusion Dependence (TD), defined as a red blood cell (RBC) transfusion requirement of ≥4 units over 8 weeks prior to study entry.
ESA relapsed or refractory to ESA or serum erythropoietin (sEPO) >500 mU/mL
Patients were non-del(5q) and lenalidomide or HMAs naive.
Patient age range from 46-83, with median of 71.5
Eastern Cooperative Oncology Group (ECOG) score PS 0-1.

Treatment:

Imetelstat sodium was administered as a 2-hour IV infusion every 4 weeks at a starting dose of 7.5 mg/kg, following premedication with an antihistamine and corticosteroid. Dose escalation to 9.4 mg/kg was permitted for insufficient response after at least 3 cycles at the initial dose, provided that ANC and platelet nadirs had not dropped below $1.5 \times 10^9$/L and $75 \times 10^9$/L, respectively, and no grade ≥3 non-hematological toxicity. Supportive care, including transfusion and myeloid growth factors as clinically indicated, was permitted.

Results

Patients

Baseline median RBC transfusion burden, 8 units/8 weeks (range: 4-14)

TABLE 15A

Treatment Exposure Parameters (N = 38)

| Median Follow-up, months (range) | 15.7 (5.6-37.5) |
|---|---|
| Initial cohort, (n = 13) | 33.7 (5.6-37.5) |
| Expansion cohort (n = 25) | 14.3 (10.9-16.5) |
| Median treatment duration, months (range) | 8.5 (0.02-37.5) |
| Median treatment cycles, (range) | 9 (1-39) |
| Median dose intensity, % | 95.2 |

The baseline characteristics are shown in Table 16 below. The following abbreviations are used in Table 16: Eastern Cooperative Oncology Group Performance Status Score of 0-1 ("ECOG PS 0-1"); refractory anemia with ringed sideroblasts ("RARS"); or refractory cytopenia with multilineage dysplasia and ringed sideroblasts ("RCMD-RS"); RAEB-1: refractory anemia with excess blasts.

TABLE 16

Baseline characteristics (N = 38)

| Median age (range), years | 71.5 (46-83) |
|---|---|
| Male, n (%) | 25 (66) |
| ECOG PS 0-1 (%) | 34 (89) |
| IPSS risk, n (%) |  |
| Low | 24 (63) |
| Intermediate-1 | 14 (37) |
| RBC transfusion burden, units/8 weeks, median (range) | 8 (4-14) |
| >4 units/8 weeks at baseline, n (%) | 35 (92) |
| WHO category, n (%) |  |
| RARS/RCMD-RS | 27 (71) |
| RA, RCMD or RAEB-1 | 11 (29) |
| sEPO > 500 mU/mL, n (%)* | 12 (32) |
| Prior ESA use, n (%) | 34 (89) |

*from 37 patients with baseline sEPO levels

Results

Exposure

Median follow-up for this analysis: 15.7 months

Median number of treatment cycles: 9 (range: 1-39 cycles)

Efficacy

Table 17 below shows key efficacy outcomes.

TABLE 17

Key Efficacy Outcomes

| Outcomes | All treated (N = 38) |
|---|---|
| Rate of ≥8-week transfusion independence (TI), n (%) | 16* (42) |
| Time to onset, weeks, median (range) | 8.3 (0.1-40.7) |
| Duration of transfusion independence (TI), weeks, median (range) | 85.9 (8.0-140.9) |
| Rate of ≥24-week transfusion independence (TI), n (%) | 11 (29) |
| Erythroid HI rate, n (%) | 26 (68) |
| ≥1.5 g/dL increase in Hgb lasting ≥8 weeks | 12 (32) |
| Transfusion reduction by ≥4 unit/8 weeks | 26 (68) |
| CR + mCR + PR (per IWG), n (%) | 9 (24) |
| CR | 5 (13) |
| marrow CR | 4 (10) |
| PR | 0 |

*additional 2 patients with 8-week transfusion independence (TI); additional 1 patient with 24-week transfusion independence (TI); additional 2 patients with CR The primary endpoint of RBC TI lasting ≥8-weeks was achieved across different subgroups as shown in Table 18:

TABLE 18

8-week transfusion independence (TI) across different subgroups

| | N | 8-week TI |
|---|---|---|
| All Subjects (%) | 38 | 16 (42.1) |
| WHO 2008 category | | |
| RARS/RCMD-RS | 27 | 12 (44.4) |
| Other | 11 | 4 (36.4) |
| RBC transfusion burden | | |
| 4-6 units | 17 | 8 (47.1) |
| >6 units | 21 | 8 (38.1) |
| IPSS risk status | | |
| Intermediate-1 | 14 | 11 (78.6) |
| Low | 24 | 5 (20.8) |
| Serum erythropoietin level | | |
| ≤500 mU/mL | 25 | 12 (48) |
| >500 mU/mL | 12 | 4 (33.3) |

Among 34 Patients with Baseline Cytogenetic Data:

6/34 (18%) had intermediate or poor cytogenetic risk (see Table 19)

5/6 (83%) achieved 8-week transfusion independence (TI) and all had a ringed-sideroblast WHO subtype 3/3 with trisomy 8 achieved 8-week transfusion independence (TI) and 2/3 achieved 24-week transfusion independence (TI)

2/3 patients with available post-treatment cytogenetic data achieved partial cytogenetic response

TABLE 19

Activity in Patients with Intermediate or Poor Cytogenetic Risk

| Subject | Karyotype | 24 wk* | 48 wk* | 24-wk TI | 48-wk TI | WHO Class |
|---|---|---|---|---|---|---|
| A | 47, XX, +8 [9] (45%) | 47, XX, +8 [1] (5%) | | X | X | RCMD-RS |
| B | 47, XY, +8 [20] (100%) | 47, XY, +8 [5] (25%) | 47, XX, +8 [1] (5%) | X | X | RCMD-RS |
| C | 47, XX, +8 [20] (100%) | | | X | | RARS |
| D | 46, XY, DEL(7) (Q22) [5] (25%) | | | X | | RCMD-RS |
| E | 46, XX, Dup/Tri/Qtp(9)(P13P24) [20] (100%) | 46, XX, Dup/Tri/Qtp(9) (P13P24) [19] (95%) | 46, XX, Dup/Tri/Qtp(9) (P13P24) [19] (95%) | X | | RCMD-RS |
| F | 46, XY, T(3; 3)(Q21; Q26.2) (100%) | | | | | RA |

*post imetelstat

TI: transfusion independence

Impact on Malignant Clone with Imetelstat

2/6 patients with baseline SF3B1 mutations had reduction in variant allele frequency and maintained transfusion independence (TI) lasting over a year (Table 20)

TABLE 20

Impact on Malignant Clone with Imetelstat

| SF3B1 mutated subject ID | TI duration in SF3B1 patients (weeks) |
|---|---|
| G | 48.7 |
| H | 3.6 |
| I | 52 |
| A | 32 |
| B | 56.7 * |
| J | 62.9 * |

* confirmed partial cytogenetic response (100% to 5% abnormal karyotype)
TI: transfusion independence Of the 16 patients who achieved 8-week transfusion independence (TI):
  Median duration of transfusion independence (TI) is 86 weeks (range: 8-141 weeks)
  11/16 (69%) achieved 24-week transfusion independence (TI) rate
  12/16 (75%) had a Hgb rise ≥3 g/dL from the pretreatment level
  Mean relative reduction of RBC transfusion burden from baseline was 68%

Safety

Adverse effects included thrombocytopenia, neutropenia and anemia (Table 21)

TABLE 21

Hematologic Adverse Events

| | All Grades N = 38 (n, %) | ≥Grade 3 N = 38 (n, %) |
|---|---|---|
| Neutropenia | 22 (58) | 21 (55) |
| Thrombocytopenia | 25 (66) | 23 (61) |
| Anemia | 10 (26) | 8 (21) |
| Alanine aminotransferase ("ALT") increased | 7 (18) | 2 (5) |
| Aspartate aminotransferase ("AST") increased | 6 (16) | 3 (8) |
| Back pain* | 7 (18) | 0 |
| Bronchitis | 6 (16) | 3 (8) |
| Other AEs+ | 6 (16) | 0 |
| Headache | 6 (16) | 1(3) |

*In 3/7 (43%) patients back pain was an AE associated with infusion related reaction
+nasopharyngitis, diarrhea, constipation, edema, peripheral and asthenia occurred in 6/38 (16%) patients with no Grade ≥3 events

TABLE 22

Reversible Grade 3/4 Cytopenias

| Laboratory Value | Grade 3/4 cytopenia (n, %) |
|---|---|
| Neutrophils, n (%) | 22/38 (58) |
| Platelets, n (%) | 24/38 (63) |

For neutrophils, 91% resolved within 4 weeks while 9% did not resolve within 4 weeks. For platelets, 92% resolved within 4 weeks while 8% did not resolve within 4 weeks. 2/38 patients (5%) had febrile neutropenia. 4/38 patients (10%) had bleeding events, 2/38(5%) were Grade 3/4.

On target activity was demonstrated by the reduction in telomerase activity and hTERT expression (Table 23). The results show that patients with transfusion independence (TI) haver higher reduction in hTERT expression (Table 24)

TABLE 23

| Biomarker reduction from baseline | TA | hTERT |
|---|---|---|
| Any reduction | 6/12 (50%) | 26/35 (74%) |
| at least 50% reduction from baseline* | 3/12 (25%) | 18/35 (51%) |

*50% reduction is the PD effect shown in the correlation with in vivo anti-tumor activity from preclinical xenograft models

TABLE 24

Patients with transfusion independence (TI) have higher reduction in hTERT expression

| hTERT reduction from baseline | 8-wk TI Response | | 24-wk TI Response | |
|---|---|---|---|---|
| | Yes | No | Yes | No |
| Any reduction | 12/15 (80%) | 14/20 (70%) | 10/11 (91%) | 16/24 (67%) |
| At least 50% reduction from baseline* | 11/15 (73%) | 7/20 (35%) | 9/11 (82%) | 9/24 (38%) |

*50% reduction is the PD effect shown in the correlation with in vivo anti-tumor activity from preclinical xenograft models Overall, 8-week TI observed in 42% of all patients, with a 24-week TI rate of 29%. The median duration of transfusion independence (TI) was 20 months. Overall, TR (HI-E) was observed in 68% of all patients.

Transfusion independence was observed across different clinical subgroups, including patients with intermediate/poor cytogenetic risk. The biomarker data suggests potential effect on the malignant clone and disease modification.

Although the particular embodiments have been described in some detail by way of illustration and example for purposes of clarity of understanding, it is readily apparent in light of the teachings of this invention that certain changes and modifications may be made thereto without departing from the spirit or scope of the appended claims.

Accordingly, the preceding merely illustrates the principles of the invention. Various arrangements may be devised which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of identifying a subject with myelodysplastic syndrome (MDS) for treatment with a telomerase inhibitor, the method comprising:
  measuring human telomerase reverse transcriptase (hTERT) expression level in a biological sample of target cells obtained from the subject after administration a telomerase inhibitor; and comparing the hTERT expression level in the biological sample to a baseline hTERT expression level prior to administration of the telomerase inhibitor;

wherein a 50% or greater reduction in hTERT expression level in the biological sample after administration of the telomerase inhibitor identifies a subject who has an increased likelihood of benefiting from treatment with the telomerase inhibitor, and wherein the telomerase inhibitor is imetelstat or a pharmaceutically acceptable salt thereof.

2. The method of claim 1, wherein the hTERT expression level measured or assessed is hTERT RNA expression level.

3. The method of claim 1, wherein the hTERT expression level measured or assessed is hTERT protein expression level.

4. The method of claim 1, wherein the imetelstat is imetelstat sodium.

5. The method of claim 1, wherein the MDS is relapsed or refractory MDS and wherein the subject is classified as a low or intermediate-1 IPSS risk MDS subject.

6. The method of claim 1, wherein the subject is transfusion dependent.

7. The method of claim 1, wherein the subject is a non-del5q human patient.

8. The method of claim 1, wherein the subject is naive to treatment with an agent selected from a hypomethylating agent (HMA) and lenalidomide.

9. The method of claim 1, wherein the subject has trisomy 8.

10. The method of claim 9, wherein the subject has trisomy 8 with mosaicism.

11. A method of treating myelodysplastic syndrome (MDS) in a subject, the method comprising:

classifying the subject as having a reduction in human telomerase reverse transcriptase (hTERT) expression level in a biological sample of target cells after administration of the telomerase inhibitor as compared to a baseline expression level prior to administration of the telomerase inhibitor, wherein a 50% or greater reduction in hTERT expression level in the biological sample after administration of the telomerase inhibitor identifies the subject as having an increased likelihood of benefiting from treatment with the telomerase inhibitor; and administering to the subject an effective amount of a telomerase inhibitor, wherein the administering is effective for treating MDS in the subject, and wherein the telomerase inhibitor is imetelstat or a pharmaceutically acceptable salt thereof.

12. The method of claim 11, wherein the hTERT expression level measured or assessed is hTERT RNA expression level.

13. The method of claim 11, wherein the hTERT expression level measured or assessed is hTERT protein expression level.

14. The method of claim 11, wherein the imetelstat is imetelstat sodium.

15. The method of claim 11, wherein the MDS is relapsed or refractory MDS.

16. The method of claim 11, wherein the MDS is MDS relapsed or refractory to erythropoiesis-stimulating agent (ESA).

17. The method of claim 11, wherein the subject is classified as a low or intermediate-1 IPSS risk MDS subject.

18. The method of claim 11, wherein the subject is transfusion dependent.

19. The method of claim 18, wherein the transfusion dependent subject has a transfusion requirement of about 4 units or more during the 8 weeks prior to the administration of the telomerase inhibitor.

20. The method of claim 11, wherein the subject is a non-del5q human patient.

21. The method of claim 11, wherein the subject is naive to treatment with an agent selected from a hypomethylating agent (HMA), lenalidomide, and combination thereof.

22. The method of claim 21, wherein the subject is naive to treatment with HMA selected from decitabine and azacitidine.

23. The method of claim 21, wherein the subject is naive to treatment with lenalidomide.

24. The method of claim 11, wherein the subject has trisomy 8.

25. The method of claim 24, wherein the subject has trisomy 8 with mosaicism.

26. The method of claim 11, further comprising altering the dosage of the telomerase inhibitor, the frequency of dosing, or the course of therapy administered to the subject.

27. The method of claim 11, wherein the telomerase inhibitor is administered for 1, 2, 3, 4, 5, 6, 7, 8 or more than 8 dosage cycles, each cycle comprising:

intravenous administration of about 7-10 mg/kg imetelstat once every four weeks;

intravenous administration of about 7-10 mg/kg imetelstat once weekly for four weeks;

intravenous administration of about 2.5-10 mg/kg imetelstat once every three weeks; or intravenous administration of about 0.5-9.4 mg/kg imetelstat once every four weeks.

28. The method of claim 27, wherein each dosage cycle comprises intravenous administration of about 7-10 mg/kg imetelstat once every four weeks.

29. A method of monitoring therapeutic efficacy in a subject with myelodysplastic syndrome (MDS), the method comprising:

measuring human telomerase reverse transcriptase (hTERT) expression level in a biological sample of target cells obtained from the subject after administration of a telomerase inhibitor; and comparing the hTERT expression level in the biological sample to a baseline hTERT expression level prior to administration of the telomerase inhibitor;

wherein a 50% or greater reduction in hTERT expression level in the biological sample after administration of the telomerase inhibitor identifies a subject who has an increased likelihood of benefiting from treatment the telomerase inhibitor, and wherein the telomerase inhibitor is imetelstat or a pharmaceutically acceptable salt thereof.

30. The method of claim 29, wherein the imetelstat is imetelstat sodium.

31. The method of claim 29, wherein the subject is transfusion dependent.

32. The method of claim 29, wherein the subject has trisomy 8.

33. The method of claim 32, wherein the subject has trisomy 8 with mosaicism.

34. A method of identifying and treating a subject with myelodysplastic syndrome (MDS) with a telomerase inhibitor, the method comprising:

diagnosing the subject with trisomy 8, wherein the diagnosis of trisomy 8 in the subject identifies the subject having an increased likelihood of benefitting from treatment with the telomerase inhibitor; and administering to the subject with trisomy 8 an effective amount of the telomerase inhibitor;

wherein the administering is effective for treating MDS in the subject, and wherein the telomerase inhibitor is imetelstat or a pharmaceutically acceptable salt thereof.

35. The method of claim 34, wherein the imetelstat is imetelstat sodium.

36. The method of claim 34, wherein the subject is naive to treatment with an agent selected from a hypomethylating agent (HMA), lenalidomide, and combination thereof.

37. The method of claim 34, wherein the subject is transfusion dependent.

38. A method of treating myelodysplastic syndrome (MDS), the method comprising:

administering to a subject in need thereof an effective amount of a telomerase inhibitor, wherein the subject is diagnosed as having trisomy 8, wherein the diagnosis of trisomy 8 in the subject identifies the subject having an increased likelihood of benefitting from treatment with the telomerase inhibitor, and wherein the telomerase inhibitor is imetelstat or a pharmaceutically acceptable salt thereof.

39. The method of claim 38, wherein the imetelstat is imetelstat sodium.

40. The method of claim 38, wherein the MDS is relapsed or refractory MDS.

41. The method of claim 38, wherein the MDS is MDS relapsed or refractory to erythropoiesis-stimulating agent (ESA).

42. The method of claim 38, wherein the subject is classified as a low or intermediate-1 IPSS risk MDS subject.

43. The method of claim 38, wherein the subject is transfusion dependent.

44. The method of claim 43, wherein the transfusion dependent subject has a transfusion requirement of about 4 units or more during the 8 weeks prior to the administration of the telomerase inhibitor.

45. The method of claim 38, wherein the subject is a non-del5q human patient.

46. The method of claim 38, wherein the subject is naive to treatment with an agent selected from a hypomethylating agent (HMA), lenalidomide, and combination thereof.

* * * * *